(12) United States Patent
Tajima et al.

(10) Patent No.: US 9,466,040 B2
(45) Date of Patent: Oct. 11, 2016

(54) AUTOMATIC ANALYSIS SYSTEM AND DEVICE MANAGEMENT SERVER

(75) Inventors: Yoshiyuki Tajima, Fujisawa (JP); Takashi Noguchi, Machida (JP); Shigeru Yano, Hitachinaka (JP); Koji Kamoshida, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 354 days.

(21) Appl. No.: 13/697,741

(22) PCT Filed: Mar. 25, 2011

(86) PCT No.: PCT/JP2011/057422
§ 371 (c)(1),
(2), (4) Date: Jan. 24, 2013

(87) PCT Pub. No.: WO2011/142182
PCT Pub. Date: Nov. 17, 2011

(65) Prior Publication Data
US 2013/0117042 A1 May 9, 2013

(30) Foreign Application Priority Data
May 14, 2010 (JP) .................................. 2010-111913

(51) Int. Cl.
*G06Q 10/00* (2012.01)
*G06Q 10/06* (2012.01)
*G01N 35/00* (2006.01)
*G06Q 50/22* (2012.01)

(52) U.S. Cl.
CPC ... *G06Q 10/063114* (2013.01); *G01N 35/0092* (2013.01); *G01N 35/0095* (2013.01); *G06Q 50/22* (2013.01)

(58) Field of Classification Search
CPC .............................. G06Q 50/22; G06Q 50/24
USPC ..................................................... 705/2, 3, 4
See application file for complete search history.

(56) References Cited

U.S. PATENT DOCUMENTS

| | | | |
|---|---|---|---|
| 5,358,691 A * | 10/1994 | Clark et al. ..................... 422/64 |
| 5,576,215 A * | 11/1996 | Burns et al. .................... 436/50 |
| 5,988,857 A * | 11/1999 | Ozawa et al. ................ 700/213 |
| 6,594,537 B1 * | 7/2003 | Bernstein et al. ............ 700/100 |
| 2003/0120633 A1 * | 6/2003 | Torre-Bueno ......... G06F 19/366 |

(Continued)

FOREIGN PATENT DOCUMENTS

| JP | 10-034499 A | 2/1998 |
|---|---|---|
| JP | 10-062426 A | 3/1998 |

(Continued)

*Primary Examiner* — Jonathan K Ng
(74) *Attorney, Agent, or Firm* — Volpe and Koenig, P.C.

(57) ABSTRACT

Precise prediction of the state of congestion in an automatic analysis system and adjustment of timings and the order of take-in and take-out of specimens in each of devices prevent increase in TATs of urgent specimens. A device management server for instructing each device to take in or take out specimens in each device determines the current position of each specimen, estimates the staying time of each specimen in one of regions by simulating the operation of each device assuming an initial state in which each specimen is at the current position, causes the simulation unit to perform a simulation, and corrects the timings or order of take-in and take-out of one or more other specimens so that each of the staying times in one of the regions do not exceed a corresponding allowable staying time in the region.

10 Claims, 26 Drawing Sheets

(56) References Cited

U.S. PATENT DOCUMENTS

| | | | |
|---|---|---|---|
| 2003/0183683 A1* | 10/2003 | Stewart | G06F 19/366 235/376 |
| 2009/0316977 A1* | 12/2009 | Juncker | G06F 19/366 382/133 |
| 2010/0063847 A1* | 3/2010 | Eisenberg | A61B 10/0096 705/3 |
| 2010/0088116 A1* | 4/2010 | Eisenberg | A61B 10/00 705/3 |
| 2013/0110534 A1* | 5/2013 | Iasella | G06Q 50/22 705/2 |
| 2014/0117080 A1* | 5/2014 | Schwarz | G06F 19/366 235/375 |

FOREIGN PATENT DOCUMENTS

| | | | |
|---|---|---|---|
| JP | 2000-046839 A | 2/2000 | |
| JP | 2008-039552 A | 2/2008 | |
| JP | 2010-107403 A | 5/2010 | |
| JP | 2010-236962 A | 10/2010 | |
| WO | WO 2008/110581 * | 9/2008 | G01N 33/68 |

\* cited by examiner

| PATIENT ID (T701) | SPECIMEN ID (T702) | ITEM GROUP ID (T703) | PRIORITY (T704) |
|---|---|---|---|
| ⋮ | ⋮ | ⋮ | ⋮ |

| DEVICE ID (T801) | WAIT REGION ID (T802) | ALLOWABLE WAIT TIME (T803) |
|---|---|---|
| ⋮ | ⋮ | ⋮ |

| DEVICE ID (D2811) | WAIT REGION ID (D2812) | QUEUE ORDER (D2813) | SPECIMEN ID (D2814) |
|---|---|---|---|
| ⋮ | ⋮ | ⋮ | ⋮ |

(b)
D282

| DEVICE ID (D2821) | TIME (D2822) | SPECIMEN ID (D2823) | INDICATION VALUE (D2824) |
|---|---|---|---|
| ⋮ | ⋮ | ⋮ | ⋮ |

(c)
D283

| TIME (D2831) | DEVICE ID (D2832) | WAIT REGION ID (D2833) | SPECIMEN ID (D2834) | WAIT TIME (D2835) |
|---|---|---|---|---|
| ⋮ | ⋮ | ⋮ | ⋮ | ⋮ |

(d)
D284

| DEVICE ID (D2841) | TIME (D2842) | SPECIMEN ID (D2843) | INDICATION VALUE (D2844) |
|---|---|---|---|
| ⋮ | ⋮ | ⋮ | ⋮ |

FIG. 20

SCREEN FOR REGISTERING SCHEDULING PARAMETERS

| ITEM GROUP | REPRESENTATIVE SPECIMEN | SHORTEST PROCESSING TIME | ALLOWABLE DELAY TIME |
|---|---|---|---|
| BIOCHEMISTRY GENERAL 1 ▽ | SECONDARY 1 ▽ | 15 MINUTES | 5 MINUTES ▽ |
| G101 | G103 | G104 | G105 |

FLOW VIEW

| STORAGE | INPUT | CENTRIFUGE | DECAP | ALIQUOT | LINEAR | COLORIMETRIC |
|---|---|---|---|---|---|---|
| ID=PRIMARY | | | | | | ID=SECONDARY 1 |

G102

OK   Cancel
G106  G107

FIG. 27

```
Start
  ↓
OBTAIN STATES OF CONGESTION IN ADJACENT DEVICES — S701
  ↓
SET PRIORITY ORDER OF QUEUES — S702
  ↓
SolveBlock PROCESS — S703
  ↓
End
```

| PREFERRED DIRECTION OF TAKE-IN \ BLOCK | BLOCK 1 (QUEUE 1 OR 5) | BLOCK 2 (QUEUE 2 OR 6) | BLOCK 3 (QUEUE 3 OR 7) | BLOCK 4 (QUEUE 4 OR 8) |
|---|---|---|---|---|
| NO PRIORITY | QUEUE 5 | QUEUE 6 | QUEUE 7 | QUEUE 8 |
| LEFT-SIDE FIRST | QUEUE 1 | QUEUE 6 | QUEUE 7 | QUEUE 8 |
| LOWER-SIDE FIRST | QUEUE 5 | QUEUE 2 | QUEUE 7 | QUEUE 8 |
| RIGHT-SIDE FIRST | QUEUE 5 | QUEUE 6 | QUEUE 3 | QUEUE 8 |
| UPPER-SIDE FIRST | QUEUE 5 | QUEUE 6 | QUEUE 7 | QUEUE 4 |

| DEVICE ID | TIME | SPECIMEN ID | INDICATION VALUE |
|---|---|---|---|
| INPUT 1 | 9:00:00 | E2 | TAKE-IN |
| INPUT 1 | 9:00:04 | E5 | TAKE-IN |
| INPUT 1 | 9:00:08 | E6 | TAKE-IN |
| INPUT 1 | 9:00:12 | S1 | TAKE-IN |
| INPUT 1 | 9:00:16 | S3 | TAKE-IN |
| INPUT 1 | 9:00:20 | S4 | TAKE-IN |
| INPUT 1 | 9:00:24 | S7 | TAKE-IN |
| INPUT 1 | 9:00:28 | S8 | TAKE-IN |
| INPUT 1 | 9:00:32 | S9 | TAKE-IN |

(b) 3102

| DEVICE ID | TIME | SPECIMEN ID | INDICATION VALUE |
|---|---|---|---|
| INPUT 1 | 9:00:00 | E2 | TAKE-IN |
| INPUT 1 | 9:00:04 | E5 | TAKE-IN |
| INPUT 1 | 9:00:08 | E6 | TAKE-IN |
| INPUT 1 | 9:00:12 | S1 | TAKE-IN |
| INPUT 1 | 9:00:16 | S3 | TAKE-IN |
| INPUT 1 | 9:00:20 | S4 | TAKE-IN |
| INPUT 1 | 9:00:26 | S7 | TAKE-IN |
| INPUT 1 | 9:00:30 | S8 | TAKE-IN |
| INPUT 1 | 9:00:34 | S9 | TAKE-IN |

(c) 3103

| DEVICE ID | TIME | SPECIMEN ID | INDICATION VALUE |
|---|---|---|---|
| INPUT 1 | 9:00:00 | E2 | TAKE-IN |
| INPUT 1 | 9:00:04 | E5 | TAKE-IN |
| INPUT 1 | 9:00:08 | E6 | TAKE-IN |
| INPUT 1 | 9:00:12 | S1 | TAKE-IN |
| INPUT 1 | 9:00:16 | S3 | TAKE-IN |
| INPUT 1 | 9:00:20 | S4 | TAKE-IN |
| INPUT 1 | 9:00:28 | S7 | TAKE-IN |
| INPUT 1 | 9:00:32 | S8 | TAKE-IN |
| INPUT 1 | 9:00:36 | S9 | TAKE-IN |

AUTOMATIC ANALYSIS SYSTEM AND DEVICE MANAGEMENT SERVER

TECHNICAL FIELD

The present invention relates to an automatic analysis system for clinical laboratory testing, and in particular to a technology for testing urgent specimens in a determined time.

BACKGROUND ART

In the service of examining specimens such as blood and urine of patients, speedup in the service operations is demanded.

In particular, for urgent specimens (e.g., specimens for testing before diagnosis or for emergency cases), a target TAT (Turn Around Time), which is the time until output of an examination result after arrival of a specimen at a laboratory, is currently 20 to 30 minutes.

Automatic analysis systems which automatically perform operations of examining specimens each include: a group of devices for performing preprocessing such as centrifugation, decapping, and aliquoting; an analyzer group for performing analysis according to test items; a group of devices for performing postprocessing such as sorting, storing, and disposal; a transfer system providing transfer paths which interconnect the devices; a server managing the devices; a server managing test information; and an operations terminal for laboratory technicians (in charge of testing) to request testing, to manage test results, and to make settings of the groups of devices. The automatic analysis systems automatically examine various specimens inputted, according to requests for testing.

In addition, in the common automatic analysis systems, multiple inlets having different priorities are arranged in an input device through which specimens are inputted, so that urgent specimens inputted through the inlets having higher priorities can be processed in preference to the normal specimens.

However, in the time zones such as the morning of a new week in which many test requests are issued, congestion occurs, where the devices and the transfer paths are clogged with a lot of specimens because of insufficient processing capability of part of the devices. Therefore, the TATs of all the specimens including the urgent specimens greatly increase.

In order to overcome the above problem, the patent literature 1 for example, discloses a technique in which the states of existence of specimens in the transfer paths and buffers in the respective devices are monitored by use of sensors, and input of specimens is suppressed so that the transfer paths are not clogged with the specimens.

PRIOR ART LITERATURE

Patent Literature

Patent Literature 1:
Japanese Patent Laid-open No. 2008-39552

DISCLOSURE OF THE INVENTION

Problem to be Solved by the Invention

Nevertheless, interference between specimens in the downstream parts of the transfer paths cannot be predicted by the technique disclosed in the patent literature 1 only. Therefore, for example, when the aliquot ratios of some specimens are high or when specimens required to go through multiple devices are inputted, congestion can occur around redirectors arranged on the upstream and downstream sides of an aliquoter and at branch points and confluences of the transfer paths.

In addition, in the configurations of the general automatic analysis systems, the aliquoter and the analyzers are connected on the downstream side of a centrifuge which processes several tens of specimens at once. Therefore, when overtaking of a specimen does not occur, specimens which are inputted after several tens of specimens brought into a single centrifugation process are required to wait until the centrifugation process is completed.

Thus, every centrifugation process can increase the TAT by several minutes even in the cases of urgent specimens.

On the other hand, in the case where a transfer path allowing overtaking of a specimen is provided or a specimen can be transferred through a path other than a path in which congestion occurs, it is unnecessary to suppress input of specimens even when congestion occurs in a part of each system.

However, according to the technique disclosed in the patent literature 1, input of specimens is suppressed on the basis of only the states of existence of specimens. Therefore, in some cases, it is impossible to fully exercise the processing capacity which the systems originally have.

The essential problem of the conventional techniques as above is that how an inputted specimen affects occurrence of congestion after the input and what serious congestion will occur are unknown from only the states of existence of specimens, which are obtained from the sensors.

The present invention has been made in view of the above problem, and an objective of the present invention is to precisely predict the state of congestion of specimens in each system, and prevent increase in the TATs of urgent specimens.

Means for Solving the Problem

In order to achieve the above objective, an aspect of the present invention provides an automatic analysis system including devices for performing respective steps necessary for testing of specimens, the automatic analysis system comprising:

a tracking unit for determining a current position of each specimen in the devices by using an order of take-in and take-out of the specimens input in the automatic analysis system, information on predetermined transfer routes according to details of tests, and signals of specimen detection sensors arranged in each of the devices;

a simulation unit for estimating a staying time of each specimen in one of wait regions in the devices by simulating, based on operational models of the devices, an operation of each device in accordance with a take in/out schedule plan assuming an initial state in which each specimen is at the determined current position; and a take in/out scheduling unit for producing a final take in/out schedule by: producing an initial take in/out schedule plan for taking in or taking out an urgent specimen in preference to a normal specimen; causing the simulation unit to perform a simulation in accordance with the initial schedule plan; and, when a staying time of one of the specimens in one of the wait regions exceeds an allowable staying time in a wait region concerned, correcting, in the initial take in/out schedule plan, a timing or an order of take-in and take-out of at least one of the specimens other than the specimen of which staying time exceeds the allowable staying time.

Effect of Invention

According to the present invention, the states of congestion of specimens are precisely predicted, and the timings and order of take-in and take-out of specimens in each device are controlled. Therefore, it is possible to prevent increase in the TATs of urgent specimens.

BRIEF DESCRIPTION OF THE DRAWINGS

FIG. 11 is a diagram illustrating examples of a configuration and a data structure of request information according to the first embodiment.

FIG. 12 is a diagram illustrating examples of a configuration and a data structure of scheduling parameters according to the first embodiment.

FIG. 14 is a diagram illustrating examples of a configuration and a data structure of information exchanged in the device management server according to the first embodiment, where wait region information is indicated in the part (a), a take in/out schedule plan is indicated in the part (b), congestion progress information is indicated in the part (c), and a take in/out schedule is indicated in the part (d).

FIG. 20 is a diagram illustrating an example of display of a screen for registration of scheduling parameters according to the first embodiment.

FIG. 27 is a flow chart of priority control processing of the redirector according to the second embodiment.

FIG. 28 is a diagram illustrating a data structure of and examples of data in a preferred-queue determination rule table according to the second embodiment.

FIG. 31 is an explanatory diagram illustrating an example of correction of the take in/out schedule plan according to the first embodiment, where an initial take-in schedule plan is indicated in the part (a), a take-in schedule plan which is corrected once is indicated in the part (b), and a take-in schedule plan which is corrected twice is indicated in the part (c).

BEST MODE FOR CARRYING OUT THE INVENTION

Hereinbelow, some representative modes for carrying out the present invention will be explained with reference to the drawings as needed. Through the drawings, identical constituents bear the same references, and the description of each constituent is not repeated when the constituent is repeatedly used.

<First Embodiment>

In the first embodiment, an example of an automatic analysis system having a relatively simple device configuration is explained.

<System Configuration>

Figure 1:
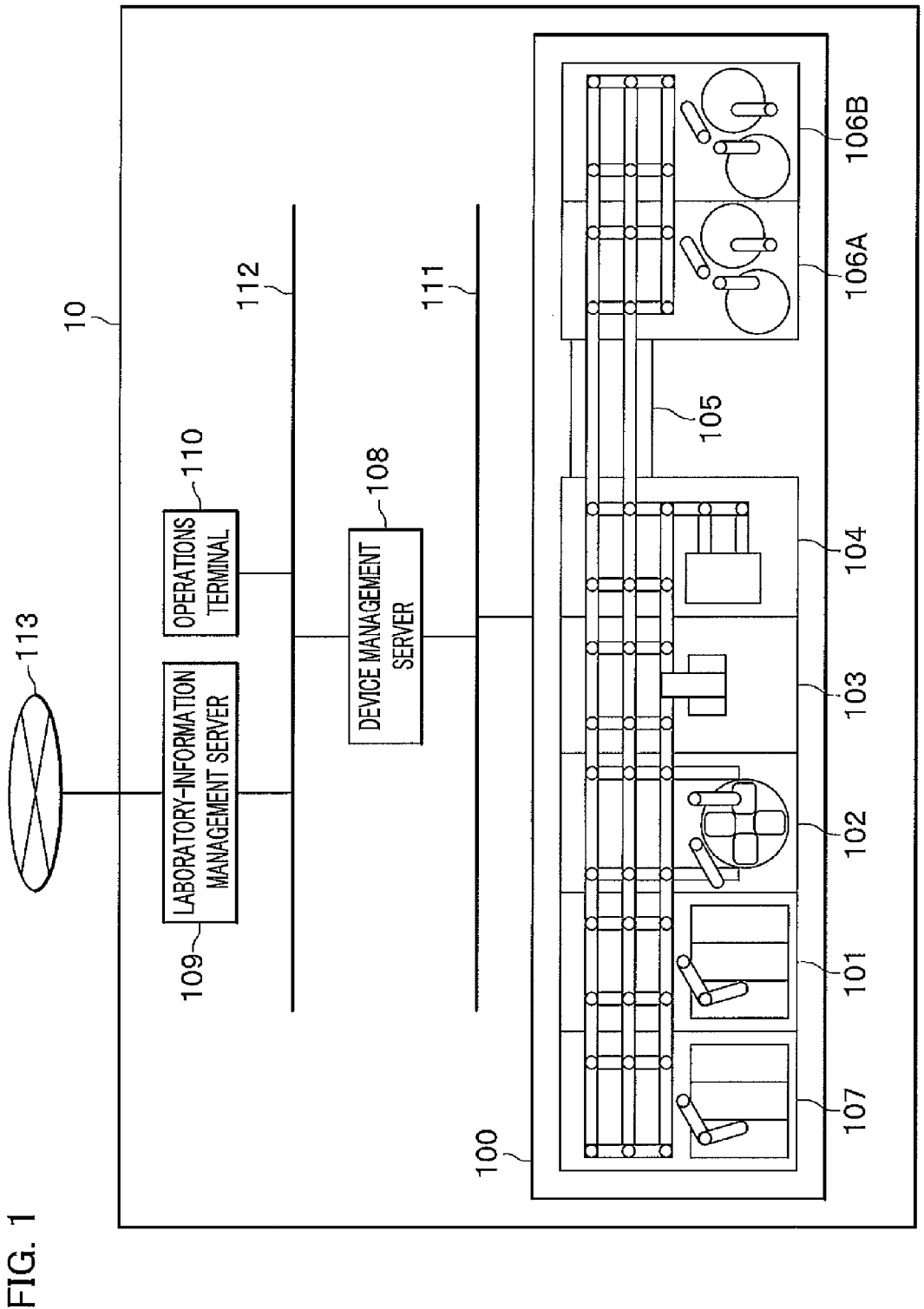
FIG. 1 is a system configuration diagram illustrating an example of an automatic analysis system according to the first embodiment.

FIG. 1 is a system configuration diagram of an automatic analysis system according to the first embodiment.

As illustrated in FIG. 1, the automatic analysis system 10 includes a testing device group 100, a device management server 108, a laboratory-information management server 109, and an operations terminal 110.

Each device in the testing device group 100 and the device management server 108 are communicably connected through a device information network 111 such as a LAN (Local Area Network), and the device management server 108, the laboratory-information management server 109, and the operations terminal 110 are communicably connected through a test-information network 112 such as a LAN.

In addition, the laboratory-information management server 109 is connected through a hospital network 113 to another system in a hospital such as an electronic medical record system.

The testing device group 100 includes an input device 101, a centrifuge 102, a decapper 103, and an aliquoter 104 as preprocessing devices, a linear conveyor 105 (as a conveyor), colorimetric analyzers 106 (A, B) as analyzers, and a storing device 107 as a postprocessing device, which are arranged as illustrated in FIG. 1.

As described later, each of the above devices includes multiple transfer paths for each device to take in and out specimens, so that specimens can be exchanged between devices by connecting transfer paths of adjacent devices.

In addition, mainly for improving the workability of the laboratory technicians, the storing device 107, which collects the specimens of which the processing is completed, is arranged at the left end so that the position at which the processed specimens are collected is close to the position at which the specimens are inputted.

Specimens to be tested, which are contained in test tubes or the like, are inputted through the input device 101, which has two inlets, one for urgent specimens and the other for normal specimens.

The urgent specimens are transferred to the centrifuge 102 in preference to the normal specimens. When no urgent specimens exist, the normal specimens are transferred to the centrifuge 102 in order of input.

When centrifugation is unnecessary, the specimens taken into the centrifuge 102 are taken out toward the decapper 103, as they are.

When centrifugation is necessary, the specimens are centrifuged in batches of several tens of specimens. Thereafter, urgent ones of the centrifuged specimens are preferentially transferred to the decapper 103.

The specimens taken into the decapper 103 from the centrifuge 102 are decapped in order of take-in, and are thereafter taken out toward the aliquoter 104.

The aliquoter 104 receives as primary specimens the specimens taken into the aliquoter 104, and produces secondary specimens in a necessary number by pipetting predetermined amounts of the primary specimens according to the type of the test.

After that, the primary specimens are transported in the reverse direction from the aliquoter 104, and collected and stored by the storing device 107. The produced secondary specimens are transported by the linear conveyor 105 to the colorimetric analyzers 106 (A, B).

The colorimetric analyzers 106 (A, B) make necessary examinations of the secondary specimens taken into the colorimetric analyzers 106 (A, B), and dispose the secondary specimens after the examinations are completed.

In the present embodiment, the preprocessing devices include the single input device 101, the single centrifuge 102, the single decapper 103, and the single aliquoter 104. However, the preprocessing devices may include more than one input device, more than one centrifuge, more than one decapper, and more than one aliquoter.

Although the conveyor includes only the linear conveyor 105 in the above configuration, the conveyor may further include one or more devices for converting the transfer direction (such as an L-shaped conveyor) or one or more buffer devices temporarily storing specimens.

Each of the colorimetric analyzers 106 (A, B) can perform analysis for multiple biochemical items. Therefore, each of the colorimetric analyzers 106 (A, B) can analyze multiple secondary specimens which are produced by aliquoting from an identical primary specimen.

Although the analyzers in the described configuration are the colorimetric analyzers 106 (A, B), the analyzers may be one or more devices which can perform analysis for other items such as electrolytes, immunities, and DNAs, and may be one or more devices which can perform analysis for multiple items at a time.

The multiple analyzers as above may include more than one type, and ones of the multiple analyzers may be connected.

Although the postprocessing device includes only the storing device 107, the postprocessing device may further include more storing devices 107 and one or more other devices such as recappers.

Each of the device management server 108 and the laboratory-information management server 109 may be provided in plurality according to the processing load and the like.

The operations terminal 110 may be provided in plurality according to the layout and the manner of use of the laboratory and other factors. Moreover, the functions of the operations terminal 110 may be performed by an operations terminal of the device management server 108 or the laboratory-information management server 109.

The layout of FIG. 1 may be changed in the present embodiment.

<Function Blocks>

Figure 2:
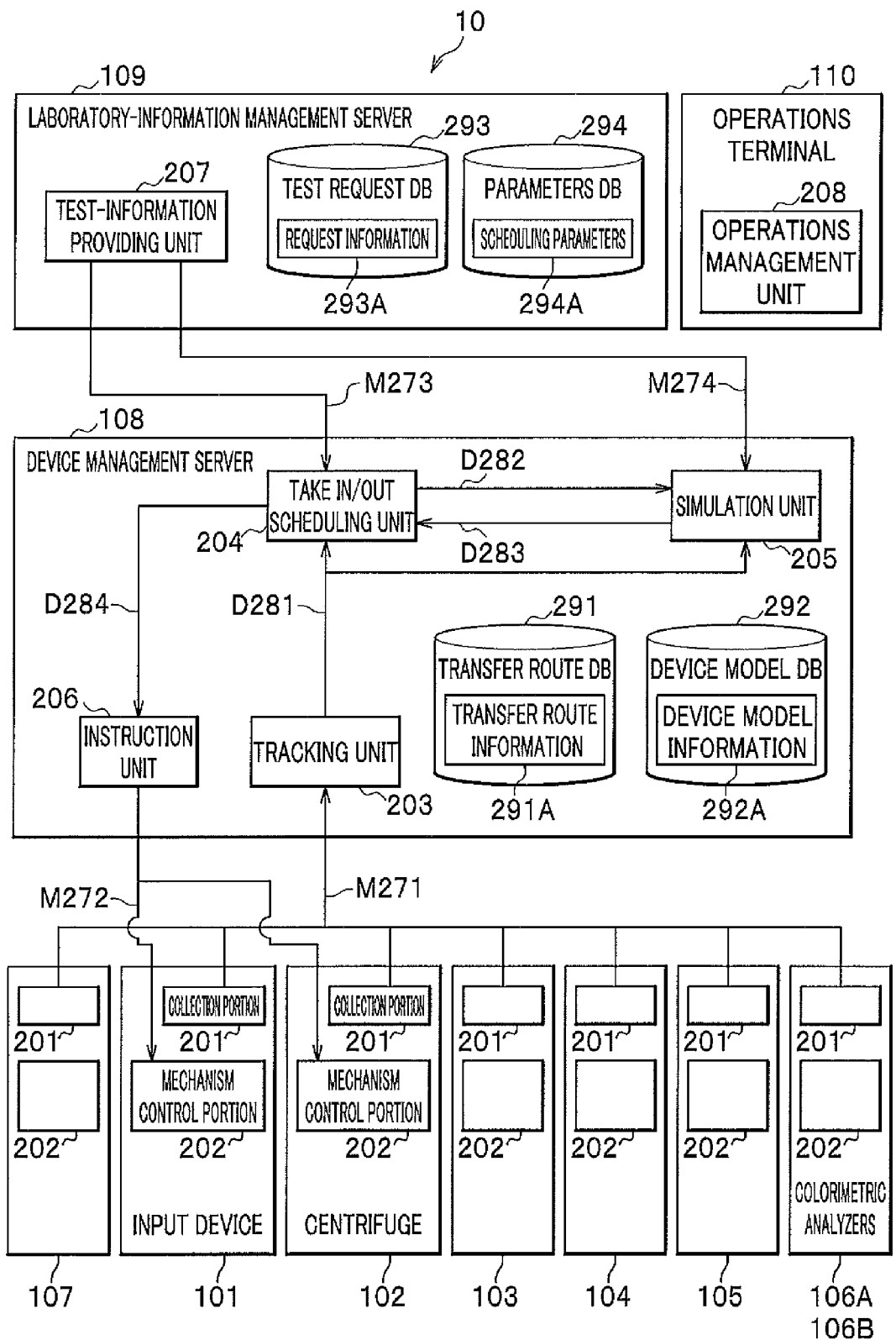
FIG. 2 is an explanatory diagram of functions and operations of the automatic analysis system according to the first embodiment.

FIG. 2 is an explanatory diagram of functions and operations of the automatic analysis system 10 according to the first embodiment.

First, the functions of the automatic analysis system 10 are explained with reference to FIG. 2.

Each of the devices as constituents of the automatic analysis system 100 (i.e., the input device 101, the centrifuge 102, decapper 103, the aliquoter 104, the linear conveyor 105, the colorimetric analyzers 106 (A, B), and the storing device 107) has a collection portion 201 and a mechanism control portion 202.

The device management server 108 has a tracking unit 203, a take in/out scheduling unit 204, a simulation unit 205, an instruction unit 206, a transfer route DB (database) 291, and a device model DB 292.

The laboratory-information management server 109 has a test-information providing unit 207, a test request DB 293, and a parameters DB 294.

In addition, the operations terminal 110 has an operations management unit 208.

<Outline of Operations>

Next, the operations of the automatic analysis system 10 are outlined with reference to FIG. 2.

Consider a case where a specimen requiring a high aliquot ratio is inputted before input of an urgent specimen, so that the processing capacity of the aliquoter 104 is exceeded, and congestion occurs in the aliquoter 104 and on the upstream side of the aliquoter 104.

The collection portion 201 in each device in the testing device group 100 transmits a sensor value M271 indicating a state of specimen detection in each of parts in the device, to the tracking unit 203 in the device management server 108.

The tracking unit 203 in the device management server 108 determines the current position of each specimen and calculates (as wait region information D281) the state of existence of one or more specimens in each of wait regions in which each specimen can stay, by use of the sensor value M271 for each device and a transfer route determined by test items for each specimen which is instructed to be taken in and out by an take in/out instruction M272.

Next, the take in/out scheduling unit 204 in the device management server 108 generates an initial take in/out schedule plan D282 in which high priority is assigned to urgent specimens, on the basis of initial condition information M273 and the wait region information D281.

Subsequently, the simulation unit 205 in the device management server 108 calculates (as congestion progress information D283) estimated amounts of the wait times in each wait region up to the lapse of a predetermined length of period from the current time in the case where specimens are taken in and out in accordance with the generated take in/out schedule plan D282, by a simulation based on processing item information M274, transfer route information 291A, and device model information 292A.

In addition, the take in/out scheduling unit 204 finally generates a take in/out schedule D284 by repeating correction of the take in/out schedule plan D282 and a simulation, where the correction of the take in/out schedule plan D282 is made by changing the timings or the order of take-in and take-out of specimens in such a manner that the estimated amounts of the wait times calculated as above do not exceed a predetermined value given by the initial condition information M273.

Finally, the instruction unit 206 transmits the take in/out instruction M272 in accordance with the produced take in/out schedule D284 to the mechanism control portions 202 in the input device 101 and the centrifuge 102.

According to the above operations, the automatic analysis system 10 can suppress the wait times in each wait region in the system to or below the predetermined value, so that the TATs of the urgent specimens can be brought within a predetermined time range.

<Transfer Mechanism>

Next, a transfer mechanism which each device in the testing device group 100 has is explained with reference to FIG. 3.

Figure 3:
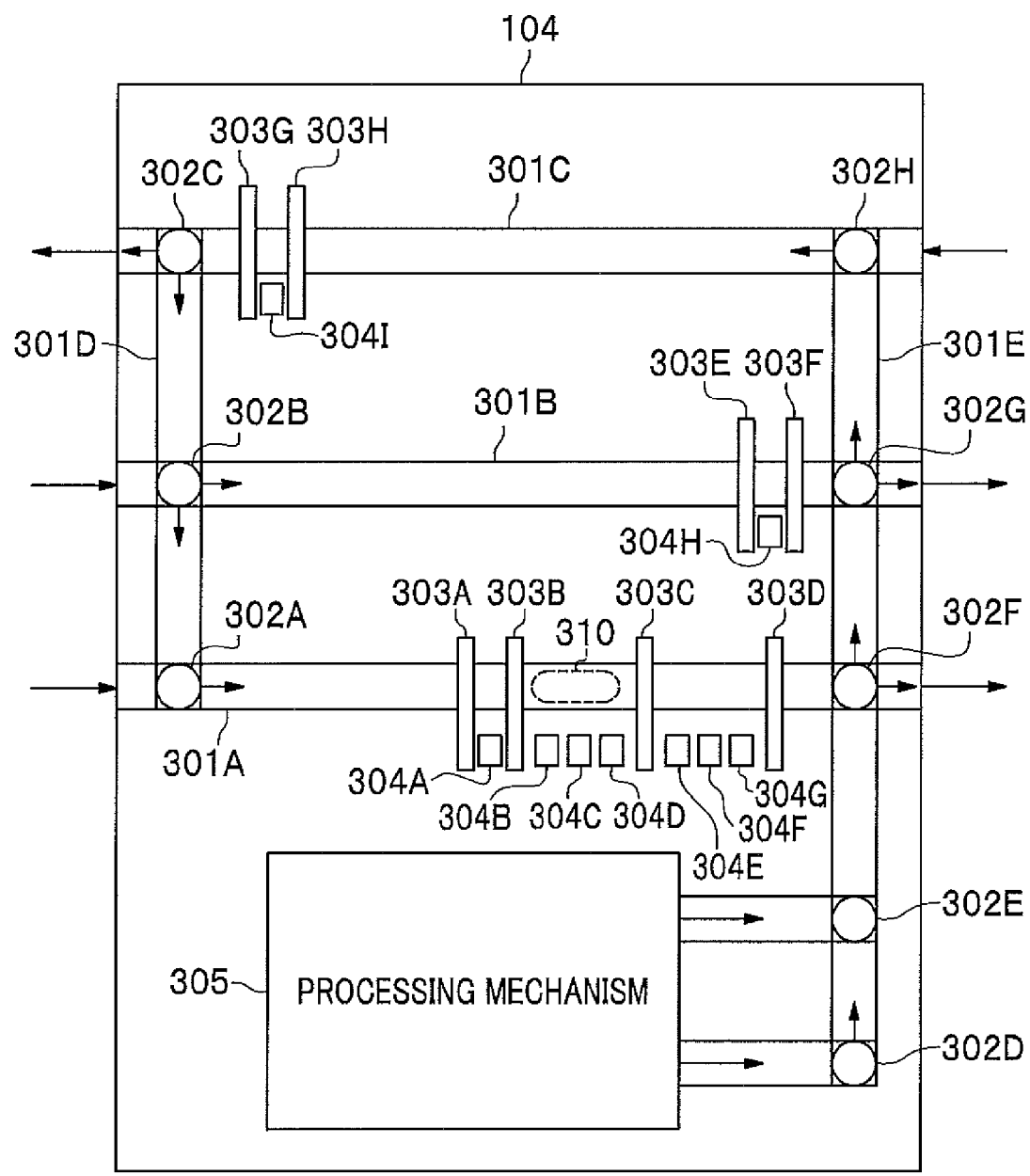
FIG. 3 is an explanatory diagram illustrating an example of a configuration of an internal mechanism of an aliquoter according to the first embodiment.

FIG. 3 illustrates as a representative example an example of a structure of an internal mechanism of the aliquoter 104.

Hereinbelow, the transfer mechanism which each device in the testing device group 100 has is explained in detail by taking the aliquoter 104 as an example.

The aliquoter 104 illustrated in FIG. 3 includes conveyor lines 301 (A to E), redirection mechanisms 302 (A to H), stoppers 303 (A to H), specimen detection sensors 304 (A to I), and a processing mechanism 305.

The conveyor lines 301 each are a mechanism which transports specimens in a predetermined direction. The conveyor lines 301A and 301B transport specimens rightward in FIG. 3, and the conveyor line 301C transports specimens leftward in FIG. 3. For example, the conveyor line 301B can be used for letting specimens not requiring aliquoting go through, and the conveyor line 301C can be used for taking out the primary specimens after the aliquoting.

The redirection mechanisms 302 are mechanisms for turning the transfer directions of specimens leftward or rightward by 90 degrees, or letting the specimens go straight, and the stoppers 303 are mechanisms for temporarily stopping specimens.

The specimen detection sensors 304 are mechanisms for detecting presence or absence of a specimen, or recognizing identification information for specimens. For example, the specimen detection sensors 304 are infrared sensors, or readers of bar codes or RFID (Radio Frequency IDentification) attached to specimens per se or racks or holders conveying the specimens.

The processing mechanism 305 is a mechanism for dispensing (aliquoting) a specimen which is stopped in the region 310 (indicated by a dashed circle on the conveyor line 301A), and is realized by, for example, feeders (feeding tubes and cups), an XYZ table, pipetters, pumps, and other components.

The aliquoter 104 produces secondary specimens in a necessary number from a primary specimen taken in from an adjacent device, by use of the processing mechanism 305, and takes out both of the primary specimen and the secondary specimens toward an adjacent device.

On that occasion, the number of specimens to be stopped and the number of specimens to be successively taken out can be controlled by changing the distances between the stoppers 303.

In addition, the operational timings of the stoppers 303 are synchronized with a device which takes in the specimens and a device which takes out the specimens, so that it is possible to prevent collision between specimens when the specimens are handed over between the devices.

In the example of FIG. 3, two conveyor lines for transferring specimens rightward, a single conveyor line for transferring specimens leftward, a single processing mechanism 305, and a single conveyor line allowing the aliquoting are arranged. However, the number of device(s) provided for each purpose may be increased or decreased according to the required capacity.

In addition, the transfer in and between the devices may be realized by use of robot arms, instead of the conveyor lines 301, the redirection mechanisms 302, and the stoppers 303.

Further, each of the input device 101, the centrifuge 102, the decapper 103, the colorimetric analyzers 106 (A, B), and the storing device 107 performing the other operations has an internal mechanism similar to that of the aliquoter 104, processes specimens taken into the device, and takes out the processed specimens toward the device in the next stage.

The linear conveyor 105 does not include a processing mechanism 305, and carries out specimens which have been carried into the linear conveyor 105, to the device in the next stage.

The aliquoter 104 is a device which processes each specimen after taking in the specimen, which is contained in a container. However, it is possible to arrange in the aliquoter 104 an external sampling device, i.e., a device for directly sampling the specimen from the linear conveyor 105 or the like, and arrange the stoppers 303 and the specimen detection sensors 304 in a part of a conveyor line in the linear conveyor 105 for setting a sampling region.

In addition, the input device 101 is configured to be able to take in specimens at any timings in an any order by using an XYZ table and a robot arm, and to be able to recognize the identification information for the specimens attached to the specimens or trays.

The centrifuge 102 is also configured to be able to take out specimens at any timings in an any order by using an XYZ table and a robot arm.

<Hardware Construction>

Figure 4:
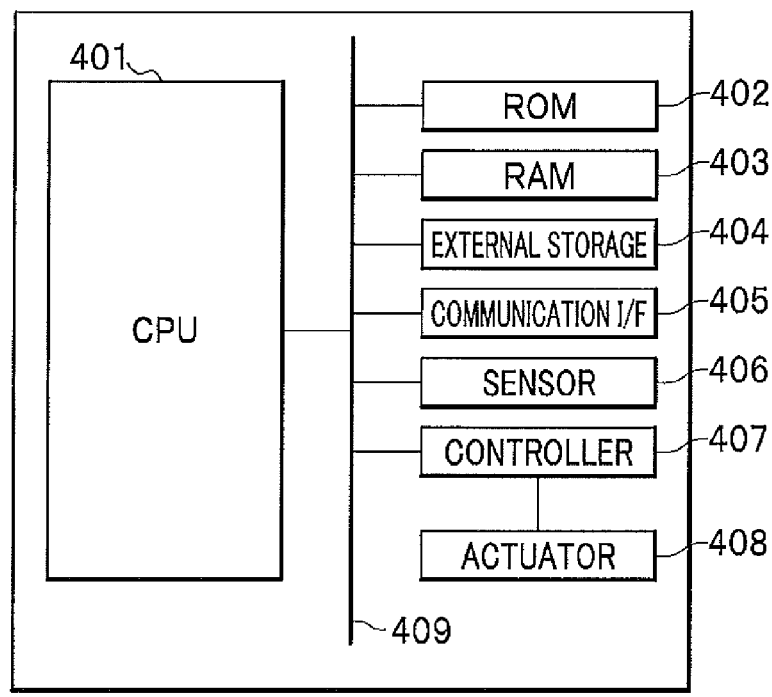
FIG. 4 is a diagram illustrating an example of a hardware construction of each device belonging to a testing device group according to the first embodiment.

FIG. 4 is a diagram illustrating an example of a hardware construction of each device in the testing device group 100.

Each device in the testing device group 100 includes a CPU (Central Processing Unit) 401 which executes programs and performs calculation, a ROM (Read Only Memory) 402 which stores basic programs such as an OS (Operating System), a RAM (Random Access Memory) 403 which is used as a temporary storage area for data to be processed, an external storage 404 such as a HDD (Hard Disk Drive) or an external memory card, a communication I/F (Interface) 405 connected to the device information network 111, various sensors 406 (including specimen detection sensors 304) for use in processing and transfer of specimens, various actuators 408 (including stoppers 303) for use in processing and transfer of specimens, and a controller 407 which controls the actuators 408. The above constituents can exchange data with each other through a CPU bus 409.

Figure 5:
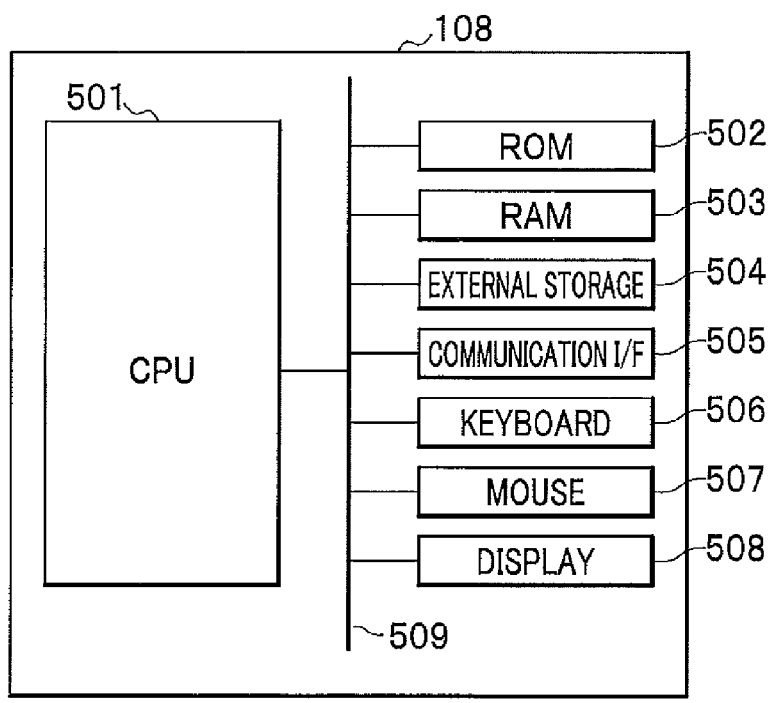
FIG. 5 is a diagram illustrating an example of a hardware construction of a device management server according to the first embodiment.

FIG. 5 is a diagram showing an example of a hardware construction of the device management server 108.

The device management server 108 includes a CPU 501 which executes programs and performs calculation, a ROM 502 which stores basic programs such as an OS, a RAM 503 which is used as a temporary storage area for data to be processed, an external storage 504 such as a HDD or an external memory card, a communication I/F 505 connected to the device information network 111 and the test-information network 112, a keyboard 506 and a mouse 507 as input devices, and a display 508 as an output device. The above constituents can exchange data with each other through a CPU bus 509.

Figure 6:
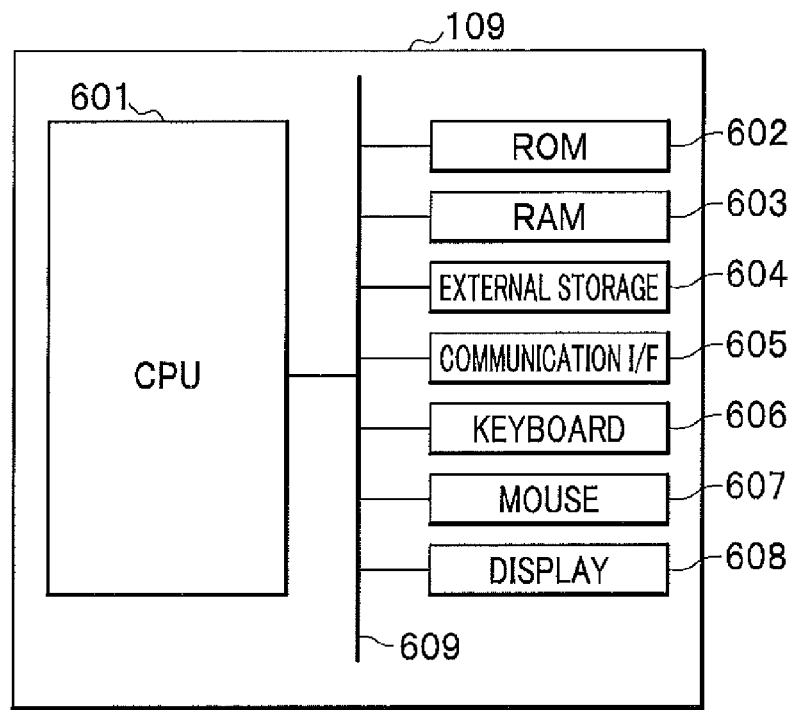
FIG. 6 is a diagram illustrating an example of a hardware construction of a laboratory-information management server according to the first embodiment.

FIG. 6 is a diagram illustrating an example of a hardware construction of the laboratory-information management server 109.

The laboratory-information management server 109 includes a CPU 601 which executes programs and performs calculation, a ROM 602 which stores basic programs such as an OS, a RAM 603 which is used as a temporary storage area for data to be processed, an external storage 604 such as a HDD or an external memory card, a communication I/F 605 connected to the test-information network 112 and the hospital network 113, a keyboard 606 and a mouse 607 as input devices, and a display 608 as an output device. The above constituents can exchange data with each other through a CPU bus 609.

Figure 7:
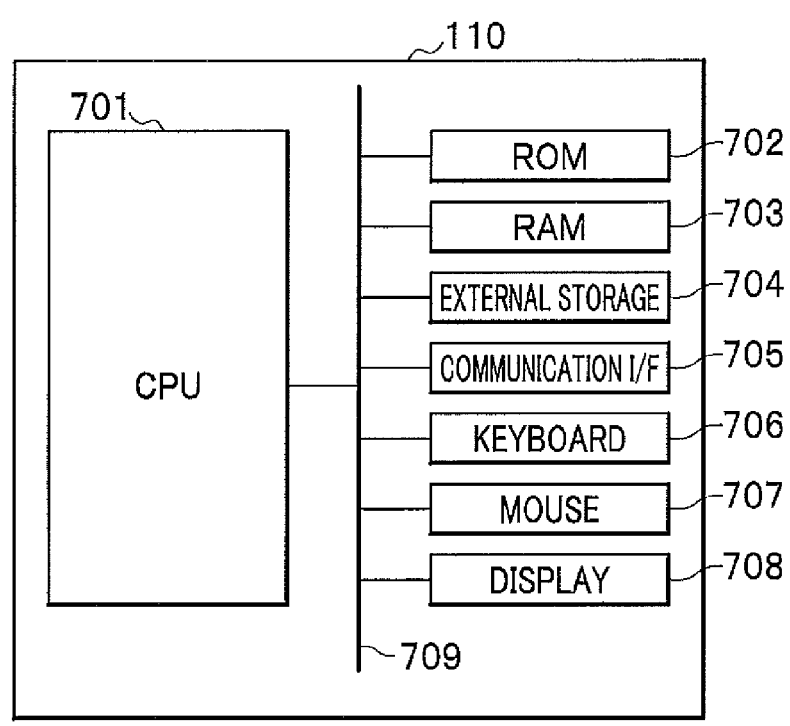
FIG. 7 is a diagram illustrating an example of a hardware construction of an operations terminal according to the first embodiment.

FIG. 7 is a diagram showing an example of a hardware construction of the operations terminal 110.

The operations terminal 110 includes a CPU 701 which executes programs and performs calculation, a ROM 702 which stores basic programs such as an OS, a RAM 703 which is used as a temporary storage area for data to be processed, an external storage 704 such as a HDD or an external memory card, a communication I/F 705 connected to the test-information network 112, a keyboard 706 and a mouse 707 as input devices, and a display 708 as an output device. The above constituents can exchange data with each other through a CPU bus 709.

<Correspondence Between Functions and Hardware>

Next, correspondence between the functions and the hardware which are arranged in each device in the automatic analysis system 10 is explained in detail with reference to FIGS. 2 and 4 to 7.

The collection region 201 and the mechanism control portion 202 in each device in the testing device group 100 are realized when the CPU 401 in the device executes the programs stored in the ROM 402, the RAM 403, or the external storage 404 and controls each of the hardware elements (the communication I/F 405, the sensor 406, the controller 407, and the actuator 408).

The tracking unit 203, the take in/out scheduling unit 204, the simulation unit 205, and the instruction unit 206 in the device management server 108 are realized when the CPU 501 executes the programs stored in the ROM 502, RAM 503, or the external storage 504, and controls each of the hardware elements (the communication I/F 505, the keyboard 506, the mouse 507, and the display 508).

The test-information providing unit 207 in the laboratory-information management server 109 is realized when the CPU 601 executes programs stored in the ROM 602, the RAM 603, or the external storage 604 and controls each of the hardware elements (the communication I/F 605, the keyboard 606, the mouse 607, and the display 608).

The operations management unit 208 in the operations terminal 110 is realized when the CPU 701 executes programs stored in the ROM 702, the RAM 703, or the external storage 704 and controls each of the hardware elements (the communication I/F705, the keyboard 706, the mouse 707, and the display 708).

Next, the functions of each device in the automatic analysis system 10 are explained in detail with reference to FIG. 2.

The collection portion 201 of each device in the testing device group 100 transmits to the tracking unit 203 of the device management server 108 the sensor value M271 related to the location of a specimen and received from the sensor 406.

The mechanism control portion 202 in each device in the testing device group 100 takes in and out specimens and processes the specimens on the basis of the take in/out instruction M272 received from the instruction unit 206 in the device management server 108.

The tracking unit 203 in the device management server 108 calculates the wait region information D281 indicating the state of stay of specimens in each wait region in each device, by using the transfer route information 291A and the sensor value M271 received from the collection portion 201 in each device in the testing device group 100.

The wait region is a region in which a specimen is stopped or decelerated for processing or transferring the specimen, or waiting for the processing or transferring.

In the mechanisms in the present embodiment, the regions immediately before the stoppers 303 can become a wait region.

The take in/out scheduling unit 204 in the device management server 108 generates the take in/out schedule plan D282 in which priority is assigned to urgent specimens, by using the wait region information D281 and the initial condition information M273 received from the test-information providing unit 207 in the laboratory-information management server 109.

In addition, the take in/out scheduling unit 204 corrects the take in/out schedule plan D282 by use of the congestion progress information D283 calculated by the simulation unit 205 (as explained later), and generates a final take in/out schedule D284.

The simulation unit 205 in the device management server 108 simulates the operation of the devices, the positions of specimens, and the state of the processing, by using the device model information 292A, the wait region information D281, the take in/out schedule plan D282, and the processing item information M274 which is received from the test-information providing unit 207 in the laboratory-information management server 109, and calculates the congestion progress information D283 (variations, with time, in the wait times in each wait region).

The instruction unit 206 in the device management server 108 transmits the take in/out instruction M272 to the input device 101, the mechanism control portion 202 in the centrifuge 102, and the like, and instructs the input device 101, the mechanism control portion 202, and the like on the order and timings of take-in and take-out of specimens, on the basis of the take in/out schedule D284.

The transfer route DB 291 in the device management server 108 stores and manages the transfer route information 291A, and the device model DB 292 in the device management server 108 stores and manages the device model information 292A.

The test-information providing unit 207 in the laboratory-information management server 109 generates initial condition information M273 and processing item information M274 on the basis of request information 293A stored in the test request DB 293 and scheduling parameters 294A stored in the parameters DB 294, and transmits the initial condition information M273 and the processing item information M274 to the take in/out scheduling unit 204 and the simulation unit 205 in the device management server 108.

The test request DB 293 in the laboratory-information management server 109 stores and manages the request information 293A, which is recorded by medical doctors and laboratory technicians using the electronic medical record system and the like.

The parameters DB 294 in the laboratory-information management server 109 stores and manages the scheduling parameters 294A, which are recorded by the medical doctors and the laboratory technicians.

The operations management unit 208 in the operations terminal 110 performs operations including input and output for recording the transfer route information 291A, the device model information 292A, the request information 293A, and the scheduling parameters 294A in the respective types of DBs and display of the state of the processing of specimens.

<Information Structure>

(Transfer Route Information)

Next, the transfer route information 291A in the automatic analysis system 10 is explained in detail with reference to FIG. 8, (a) to FIG. 8 (c).

The transfer route information 291A includes an item group definition table T100, a route definition table T200, and an item-route correspondence table T300.

Figure 8:
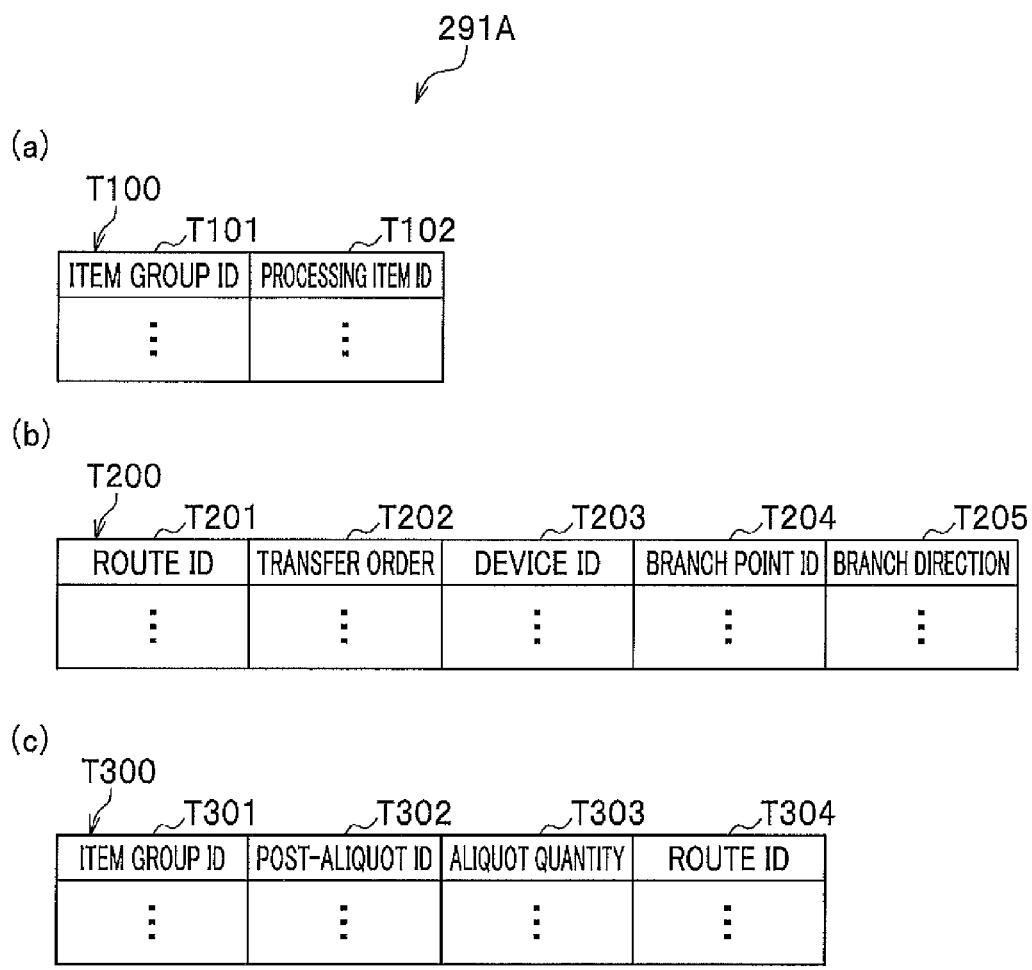
FIG. 8 is a diagram illustrating examples of a configuration and a data structure of transfer route information according to the first embodiment, where an item group definition table is indicated in the part (a), a route definition table is indicated in the part (b), and an item-route correspondence table is indicated in the part (c).

The item group definition table T100 (FIG. 8 (a)) defines an item group, and includes as attributes the item group ID (Identification) (T101) and the processing item ID (T102).

The item group ID (T101) is an identifier defining an item group including multiple items of processing to be performed on a specimen, and the processing item ID (T102) is an identifier of the items of processing to be performed on the specimen.

For example, in the case where an item group of processing items "Biochemical Processing 1" and "Biochemical Processing 3" is defined as the item group "Biochemistry General 1", two records {Biochemistry General 1, Biochemical Processing 1} and {Biochemistry General 1, Biochemical Processing 3} are registered.

Each device in the testing device group 100 processes each specimen on the basis of an item group or processing items.

For example, in the case where centrifugal separation processing for five minutes is needed to be performed on a specimen of "Biochemistry General 1", the centrifuge 102 performs centrifugal separation processing for five minutes on the basis of the item group ID for the specimen.

The route definition table T200 (FIG. 8 (b)) defines a route for transferring a specimen, and includes as the attributes the route ID (T201), the transfer order T202, the device ID (T203), the branch point ID (T204), and the branch direction T205.

The route ID (T201) is an identifier defining of a route for transferring a specimen. The transfer order T202 is consecutive numbers contained in records corresponding to an identical route ID, and indicates that the specimen is to be transferred in increasing order of the consecutive numbers. The device ID (T203) is an identifier of a device to which the specimen is to be transferred, the branch point ID (T204) is an identifier to indicate a branch point inside the device, and the branch direction T205 indicates to which direction the specimen is to be transferred.

For example, in the case where a route from the input device 101 in FIG. 1 to the aliquoter 104 is defined as "Route 1", records such as {Route 1, 1, Input, Branch Point 4, Upward}, {Route 1, 2, Input, Branch Point 5, Rightward}, {Route 1, 3, Centrifuge, Branch Point 2, Straight}, {Route 1, 4, Centrifuge, Branch Point 5, Straight}, {Route 1, 5, Uncap, Branch Point 2, Straight}, {Route 1, 6, Uncap, Branch Point 5, Straight}, and {Route 1, 7, Aliquot, Branch Point 2, Downward} are registered.

The item-route correspondence table T300 (FIG. 8 (c)) indicates the correspondences between item groups and routes, and includes as attributes the item group ID (T301), the post-aliquot ID (T302), the aliquot quantity T303, and the route ID (T304).

For example, in the case where the aliquot volume of a specimen corresponding to the item group "Biochemistry General 1" is 20 microliters, and "Route 5" is assigned to the primary specimen ("Primary"), and "Route 6" is assigned to the secondary specimen ("Secondary 1"), records such as {Biochemistry General 1, Primary, None, Route 5} and {Biochemistry General 1, Secondary 1, 20, Route 6} are registered.

In the present embodiment, the correspondences between the item groups and the routes are statistic. However, the correspondences between the item groups and the routes may be dynamically changed according to the date, time, device condition, and other factors.

(Device Model Information)

Next, the device model information 292A in the automatic analysis system 10 is explained in detail with reference to FIG. 9 (a) to FIG. 9 (d) and FIG. 10 by taking the aliquoter 104 as an example.

In addition, the other devices can also be defined in a similar manner to the aliquoter 104.

The device model information 292A is information for use in execution of a simulation by the simulation unit 205, and includes model objects T400, a state definition table T500, a state transition table T600, and a connection definition table T900.

In the following detailed explanations, the aliquoter 104 having the internal structure illustrated in FIG. 3 is taken as an example.

Figure 9:
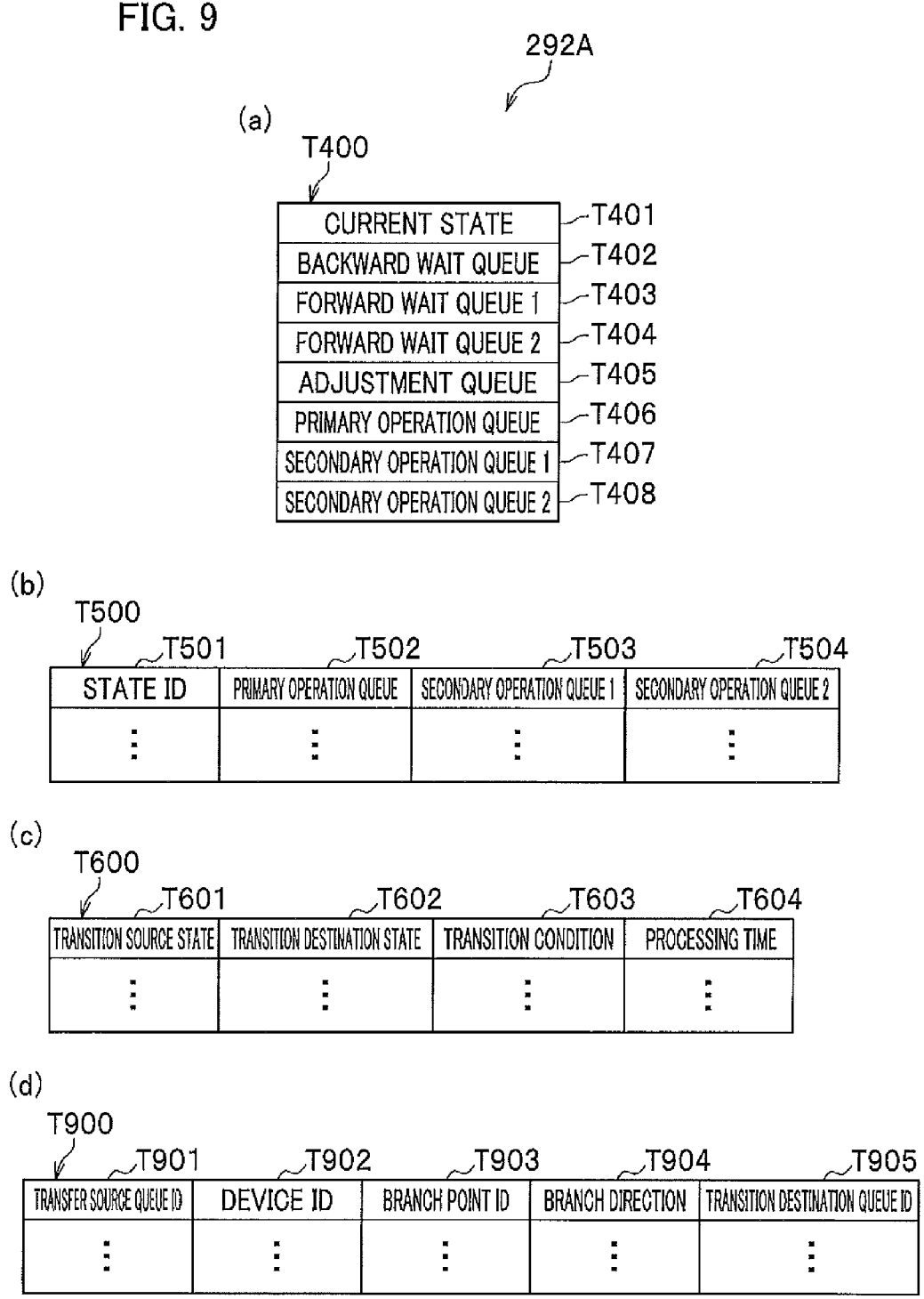
FIG. 9 is a diagram illustrating examples of a configuration and a data structure of device model information according to the first embodiment, where a model object is indicated in the part (a), a state definition table is indicated in the part (b), a state transition table is indicated in the part (c), and a connection definition table is indicated in the part (d).

Each model object T400 (FIG. 9 (a)) logically represents the state of a device, and includes as attributes the current state T and one or more queues (T402, . . . ).

The above queues are respectively in one-to-one correspondence with the wait regions in the device, and each queue is a collection (container) which holds specimen IDs in the order in which specimens are taken into the corresponding wait region, where the specimen IDs are identifiers of the specimens.

A queue ID is assigned to each queue, where the queue ID is unique in the entire automatic analysis system 10. In addition, a capacity (queue size) corresponding to the hardware specification of the device is preset, and each queue holds the number of specimens which can be taken in.

Therefore, the state of available space in each queue as a constituent of the model object T400 can be determined by appropriately storing in the queue the specimen IDs of specimens existing in the corresponding wait region.

Figure 10:
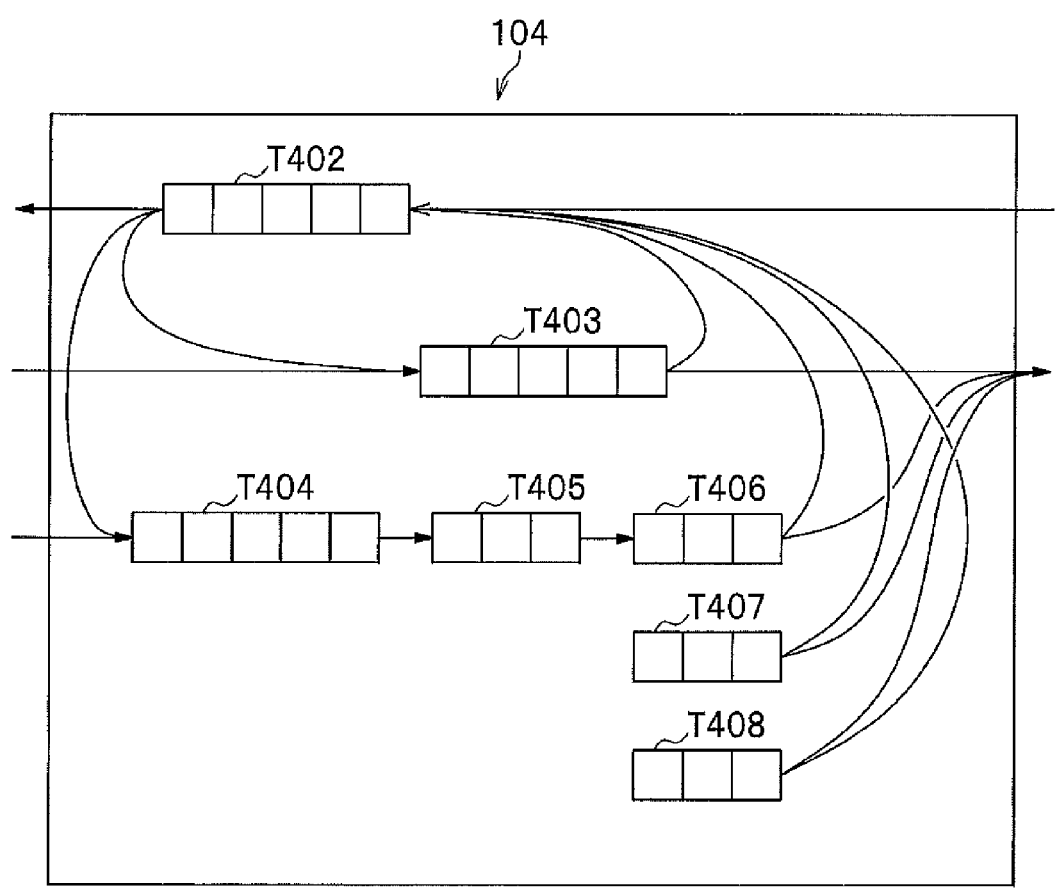
FIG. 10 is a diagram representing by a queue model an example of the internal mechanism of the aliquoter according to the first embodiment.

FIG. 10 indicates the internal mechanism of the aliquoter 104 illustrated in FIG. 3 in a queue model representation by associating a queue with each hardware element in the internal mechanism of the aliquoter 104.

FIG. 10 indicates, for example, that specimens can be transferred from the backward wait queue T402 (having the queue size of five) corresponding to the conveyor line 301C of FIG. 3 to the forward wait queue 1 (T403) (having the queue size of five) corresponding to the conveyor line 301B and the forward wait queue 2 (T404) (having the queue size of five) corresponding to the conveyor line 301A.

As indicated in FIG. 9, the model object T400 indicating the state of the aliquoter 104 (illustrated in FIG. 3) includes as attributes the current state T401 and all the queues contained in the device. The queues contained in the device include the backward wait queue T402 (having the queue size of five), the forward wait queue 1 (T403) (having the queue size of five), the forward wait queue 2 (T404) (having the queue size of five), an adjustment queue T405 (having the queue size of three), a primary operation queue T406 (having the queue size of three), a secondary operation queue 1 (T407) (having the queue size of three), and a secondary operation queue 2 (T408) (having the queue size of three).

Although FIG. 10 indicates only the connections between the queues in the aliquoter 104, connections with queues in adjacent devices are defined in the connection definition table T900 (FIG. 9 (d)), which is explained later.

As the current state T401, an identifier of the current state (state ID) is stored, where the identifier indicates which of the states defined in the state definition table T500 the current state of the device is.

The state definition table T500 (FIG. 9 (b)) defines the state of the device in correspondence with processing of specimens.

For example, the state definition table T500 for the aliquoter 104 includes as attributes the state ID (T501), the primary operation queue T502, the secondary operation queue 1 (T503), and the secondary operation queue 2 (T504).

In addition, a record such as {S0, No Specimen, No Specimen, No Specimen} is registered for an initial state (e.g., a state with the state ID=S0), in which no queue contains a specimen.

For example, a record such as {S3, 3, No Specimen, No Specimen} is registered for a state (e.g., a state with the state ID=S3) in which three specimens are taken into the primary operation queue T406.

At this time, only the queues affecting the aliquoting process (i.e., only the primary operation queue T406, the secondary operation queue 1 (T407), and the secondary operation queue 2 (T408)) are considered, and the queues not affecting the aliquoting process (i.e., the backward wait queue T402, the forward wait queue 1 (T403), the forward wait queue 2 (T404), and the adjustment queue T405 are not considered.

The state transition table T600 (FIG. 9 (c)) defines transitions of the state of the device caused by performing processing in accordance with the processing item information M274 for a specimen, and the time needed for the processing.

For example, the state transition table T600 for the aliquoter 104 includes as attributes the transition source state T601, the transition destination state T602, the transition condition T603, and the processing time T604.

For example, when the state 1 (i.e., the state with the state ID=S1) transitions to the state 2 (i.e., the state with the state ID=S2), a record such as {S1, S2, "Condition for Transition from S1 to S2", 400 (milliseconds)} is registered.

The processing time T504 is assumed to be constant in the present embodiment. However, in the case where the processing time varies with the circumstances, it is possible to add an attribute indicating a variable condition and set the processing time according to the condition, or represent the processing time as a probability distribution such as a normal distribution.

The connection definition table T900 (FIG. 9 (d)) indicates, for all the queues set in the model objects T400 for the respective devices, connections between the queues in each device and connections between queues in different devices, and includes as attributes the transfer source queue ID (T901), the device ID (T902), the branch point ID (T903), the branch direction T904, and the transition destination queue ID (T905).

In other words, when each queue defined in the model objects T400 for the devices is deemed to be a node, a record is registered for every directed edge connecting nodes.

For example, in the case where the queue 1 and the queue 2 are connected at the branch point Y in the device X, and the branch direction at the branch point is "Up", a record such as {Queue 1, Device X, Branch Point Y, Up, Queue 2} is registered.

At this time, the queue IDs stored in the transfer source queue ID (T901) and the transfer destination queue ID (T905) are the identifiers of the queues included in the model objects T400 of the devices.

In addition, the device ID (T902) and the branch point ID (T903) correspond to the device ID (T203) and the branch point ID (T204) in the route definition table T200 (see FIG. 8), so that the queues are associated with the transfer routes.

(Request Information)

Next, the request information 293A in the automatic analysis system 10 is explained in detail with reference to FIG. 11.

The request information 293A includes a test request information table T700. The test request information table T700 indicates processing items needed for testing and priorities, and includes as attributes the patient ID (T701), the specimen ID (T702), the item group ID (T703), and the priority T704.

For example, in the case where the specimen 1 (having the specimen ID=Specimen 1) obtained by blood collection from a patient 1 (having Patient ID=Patient 1) is to undergo testing of the item groups 1 and 3 with the normal priority (Priority=Normal), records such as {Patient 1, Specimen 1, Item Group 1, Normal} and {Patient 1, Specimen 1, Item Group 3, Normal} are registered.

(Scheduling Parameters)

Next, the scheduling parameters 294A in the automatic analysis system 10 are explained in detail with reference to FIG. 12.

The scheduling parameters 294A include a scheduling parameter table T800.

The scheduling parameter table T800 indicates the wait time which is allowable in each wait region in each device, and includes as attributes the device ID (T801), the wait region ID (T802), and the allowable wait time T803.

The automatic analysis system 10 generates such a take in/out schedule plan that the wait time of each of the specimens including the urgent specimens does not exceed the allowable wait time T803, and controls take-in and take-out.

Therefore, when the allowable wait time T803 is appropriately set, the TATs of the urgent specimens can always be brought within a target time range.

(Communication Information Between Devices)

Next, communication information exchanged between devices is explained with reference to FIG. 13 (a) to FIG. 13 (d).

Figure 13:
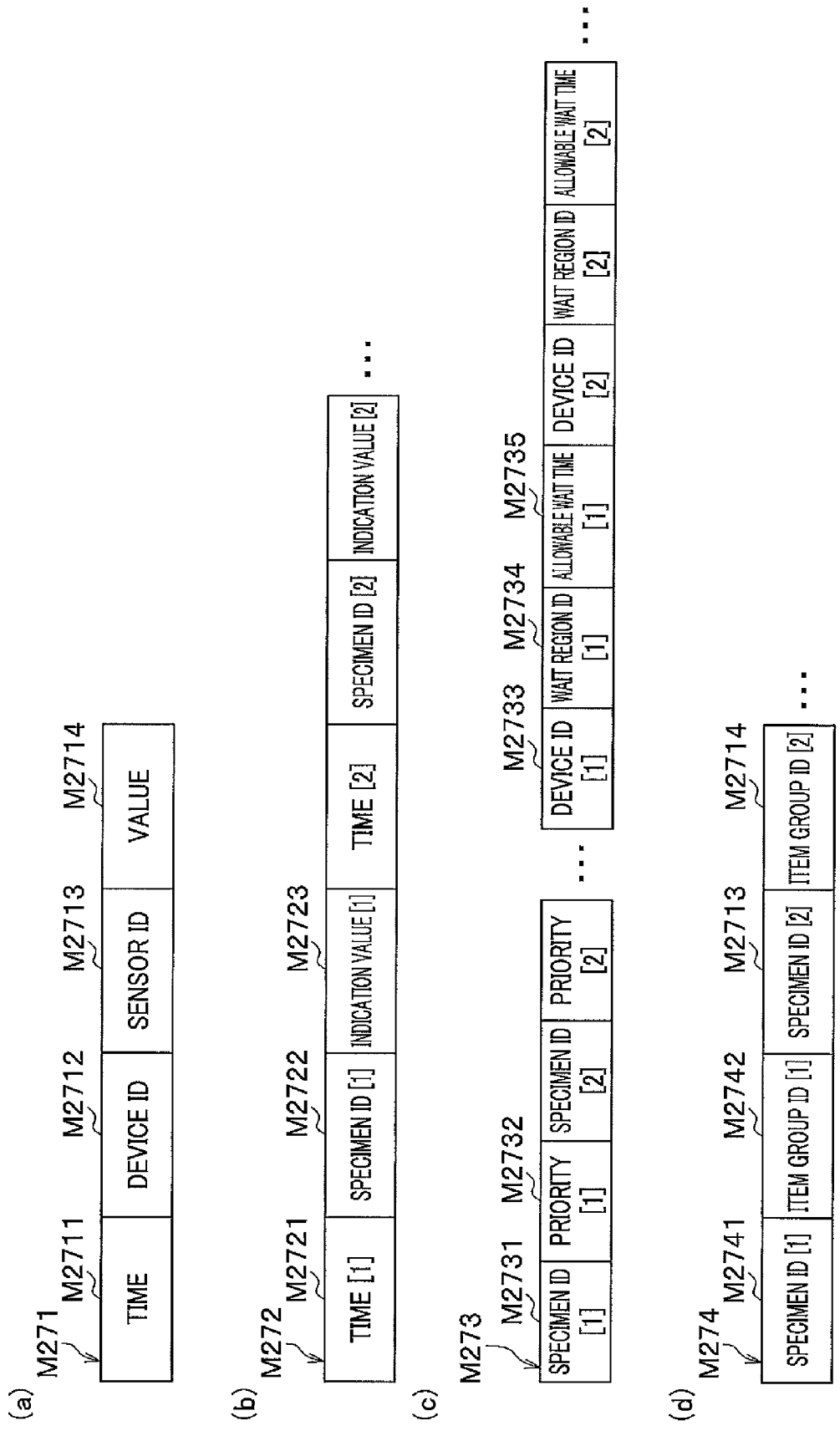
FIG. 13 is a diagram illustrating examples of a configuration and a data structure of information exchanged between subsystems in the automatic analysis system according to the first embodiment, where a sensor value is indicated in the part (a), an instruction to take in and out is indicated in the part (b), initial condition information is indicated in the part (c), and processing item information is indicated in the part (d).

The sensor value M271 (FIG. 13 (a)) indicates one of the detection results of the specimen detection sensors 304 arranged in respective parts in the devices in the testing device group 100, and includes the detection time M2711, the device ID (M2712), the sensor ID (M2713), and the value M2714.

For example, the value M2714 is a binary value indicating whether or not a specimen is on the sensor, is "1" when a specimen is on the sensor, and is "0" when no specimen is on the sensor.

Further, it is possible to configure the automatic analysis system 10 to discriminately indicate the case where a specimen exists, the case where no specimen exists and a carrier (holder or rack) for transferring a specimen exists, and the case where neither a specimen nor a carrier exists.

The take in/out instruction M272 (FIG. 13 (b)) indicates the order and timings of take-in and take-out of specimens from each device, and includes multiple sets of the time of take-in or take-out M2721, the specimen ID (M2722), and the indication value M2723 indicating take-in or take-out.

The initial condition information M273 (FIG. 13 (c)) indicates an initial condition for scheduling, and includes multiple sets of the specimen ID (M2731) and the priority M2732 and multiple sets of the device ID (M2733), the wait region ID (M2734), and the allowable wait time M2735.

The processing item information M274 (FIG. 13 (d)) indicates processing items for each specimen, and includes multiple sets of the specimen ID (M2741) and the item group ID (M2742).

(Communication Information in Device Management Server)

Next, communication information exchanged in the device management server 108 is explained with reference to FIG. 14 (a) to FIG. 14 (d).

The wait region information D281 (FIG. 14 (a)) is information indicating the state of stay of specimens and the queue order of the specimens in each wait region in the devices in the testing device group 100, and includes the device ID (D2811), the wait register (D2812), the queue order (D2813), and the specimen ID (D2814).

The queue order is represented by assigning the consecutive numbers 1, 2, 3, . . . to the specimens from the leading specimen.

The take in/out schedule plan D282 (FIG. 14 (b)) indicates a plan of the order or timings of take-in and take-out, which is produced by the take in/out scheduling unit 204. The take in/out schedule plan D282 includes the device ID (D2821), the time D2822, the specimen ID (D2823), and the indication value D2824.

The indication value D2824 indicates take-in or take-out in a similar manner to the indication value M2723 in the take in/out instruction M272.

The congestion progress information D283 (FIG. 14 (c)) is information indicating time variations of the wait time of the specimen in each wait region in a device estimated by simulation, where the wait time may include the time for processing performed on the specimen. The congestion progress information D283 includes the time D2831, the device ID (D2832), the wait region ID (D2833), the specimen ID (D2834), and the wait time D2835.

The take in/out schedule D284 (FIG. 14 (d)) indicates a plan of take-in and take-out which is finally determined by the take in/out scheduling unit 204. The take in/out schedule D284 includes the device ID (D2841), the time D2842, the specimen ID (D2843), and the indication value D2844.

The indication value D2844 indicates take-in or take-out in a similar manner to the indication value M2723 in the take in/out instruction M272.

<Processing Flow>

Next, an outline of the processing for controlling the order and timings of take-in and take-out of specimens in each device for preventing congestion with specimens in the device is explained with reference to FIG. 15.

Each device in the present embodiment performs the processing corresponding to the processing item IDs (T102) (see FIG. 8), on each specimen taken in, and takes out the processed specimen.

The device management server 108 performs the following processing, for example, every second.

Although the processing is performed every second in this example, the intervals between the performances of the processing may be shorter or longer than one second according to the processing capacity of the device management server 108 or the like.

At first (in step S101), the tracking unit 203 calculates the state of stay of specimens in each wait region (i.e., in each queue in each model object T400) on the basis of the take in/out instruction M272, the sensor value M271 received from the collection portion 201 of each device in the testing device group 100, and the transfer route information 291A, and then calculates the wait region information D281.

Subsequently (in step S102), the take in/out scheduling unit 204 calculates the state of each device according to the state definition table T500 (see FIG. 9), and makes an initial setting of each model object T400.

Thereafter (in step S103), the take in/out scheduling unit 204 issues a request to the test-information providing unit 207, and acquires the initial condition information M273.

At this time, in response to the above request, the test-information providing unit 207 generates the initial condition information M273 from the request information 293A and the scheduling parameters 294A.

Next (in step S104), the take in/out scheduling unit 204 generates the take in/out schedule plan D282 in such a manner that specimens are taken in and taken out with the maximum processing performance and the specimens for which the priority T704 is highly set in the test request information table T700 (see FIG. 11), the specimens which are loaded in the input tray or inlet for urgent specimens, and the urgent specimens which are suddenly inputted take precedence.

A concrete example of production of a take-in schedule plan for the input device 101, as part of the take in/out schedule plan D282, is explained in detail with reference to FIG. 30 (a) and FIG. 30 (b).

In this example, it is assumed that the device ID "Input 1" is assigned to the input device 101, that the input device 101 has three types of trays (a tray 3001A for urgent specimens, a tray 3001B for normal specimens, and a tray 3001C for specimens not undergoing centrifugation), and that specimens can be inputted from an arbitrary tray at the rate of one specimen every four seconds at the highest.

Figure 30:
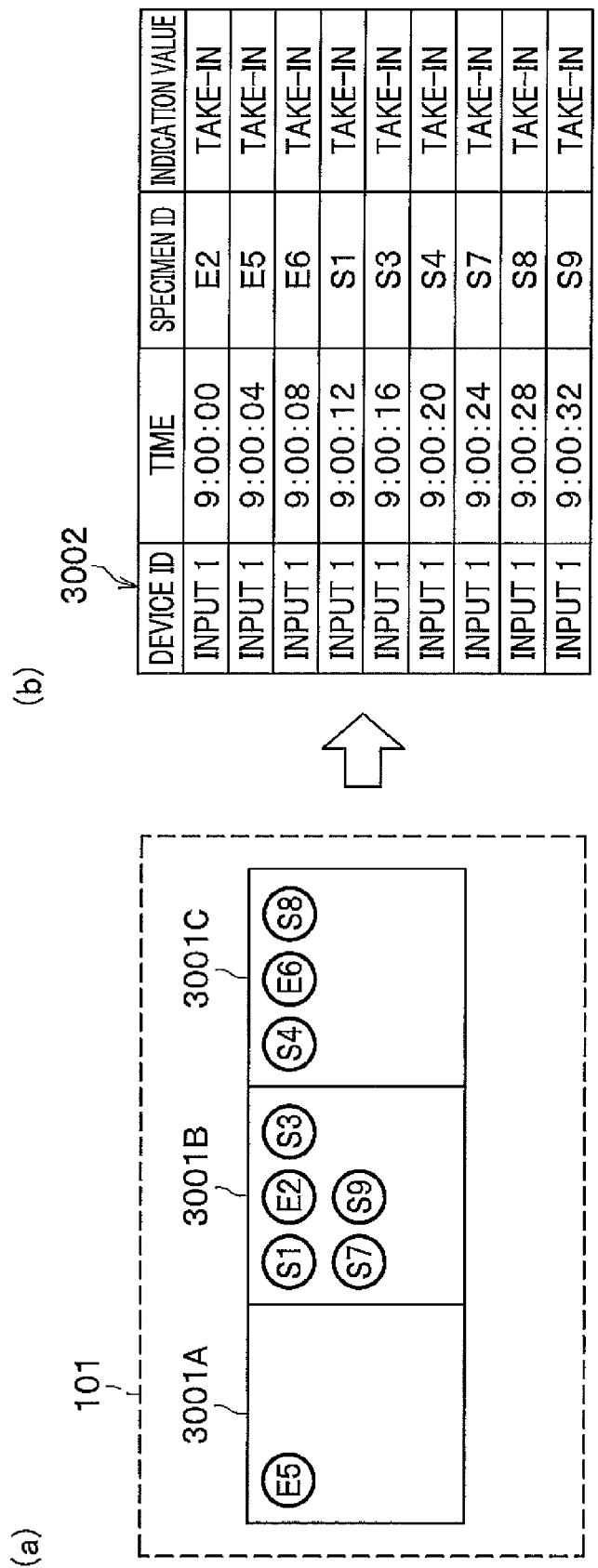
FIG. 30 is an explanatory diagram illustrating an example of production of an initial take in/out schedule plan according to the first embodiment, where an example of mounting of specimens on each tray in the input device is indicated in the part (a), and a produced take-in schedule plan is indicated in the part (b).

In addition, it is assumed that at the current time 9:00:00, one specimen (E5) is placed on the tray 3001A for urgent specimens, five specimens (S1, E2, S3, S7, S9) are placed on the tray 3001B for normal specimens, and three specimens (S4, E6, S8) are placed on the tray 3001C for specimens which are not to undergo centrifugation, as illustrated in FIG. 30 (a).

In FIG. 30, normal specimens are indicated with symbols including S (Standard), and urgent specimens are indicated with symbols including E (Emergency).

In addition, the number following S or E in each symbol indicates the order in which the specimen reaches the tray.

The initial take in/out schedule plan D282 generated at this time as above includes information as the take-in schedule plan 3002 (FIG. 30 (b)).

That is, the order of take-in is planned in such a manner that urgent specimens are preferentially taken in in order of arrival, and thereafter normal specimens are taken in in order of arrival.

The times of take-in are planned in such a manner that specimens are taken in at the maximum processing speed of the input device 100, specifically at the rate of one specimen every four seconds.

Referring back to FIG. 15, the simulation unit 205 issues a request to the test-information providing unit 207, and acquires the processing item information M274 (in step S105).

At this time, in response to the above request, the test-information providing unit 207 generates the processing item information M274 from the request information 293A.

Next (in step S106), the simulation unit 205 calculates (simulates) a state transition or transitions during the ten-minute period starting from the current time, by use of the current state of each device, the processing items for each specimen, the state transition table for each device, and the like, and calculates the congestion progress information D283 in which the wait time of each specimen is estimated, for example, at intervals of 100 milliseconds.

Although the state transition during the ten-minute period starting from the current time is calculated in the present embodiment, the period for which the state transition is calculated may be shorter or longer than ten minutes according to the processing performance of the device management server 108.

Similarly, although the wait time of each specimen is estimated at intervals of 100 milliseconds in the present embodiment, the intervals may be set shorter or longer than 100 milliseconds.

Subsequently (in step S107), the simulation unit 205 determines whether or not the wait times D2835 of all the specimens in the congestion progress information D283 are equal to or lower than the allowable wait times M2735, respectively, which are predetermined values in the initial condition information M273.

When it is determined that the wait times of all urgent specimens are equal to or lower than the predetermined value (i.e., when yes is determined in step S107), the operation goes to step S109.

When it is determined that the wait time of at least one urgent specimen is higher than the predetermined value (i.e., when no is determined in step S107), the operation goes to step S108.

In step S108, the take in/out scheduling unit 204 goes back to immediately before the take-in or take-out of the specimen of which wait time exceeds the allowable wait time earliest, generates a new take in/out schedule plan D282 by delaying and correcting the times of take-in and take-out of specimens (in step S108), and performs the processing in step S106 and the following steps again. Details of the processing in step S108 are explained later.

When the wait times of all urgent specimens are equal to or lower than the predetermined value (i.e., when yes is determined in step S107), the take in/out scheduling unit 204 passes to the instruction unit 206 the contents of the current take in/out schedule plan D282 as a final take in/out scheduling D284, and the instruction unit 206 transmits the take in/out instruction M272 instructing take-in and take-out of specimens to the mechanism control portion 202 of a corresponding one or ones of the devices in the testing device group 100. Thus, the processing of FIG. 15 is completed (in step S109).

The mechanism control portion 202 which is instructed to take in and out the specimens performs control of the mechanism so as to take in and out the specimens in accordance with the instruction.

Next, processing (in step S101 in FIG. 15) for calculating which wait region each specimen is located in is explained in detail with reference to FIG. 16. In this example, the above processing is assumed to be asynchronously performed for each wait region.

First, the tracking unit 203 performs the processing in step S202 and the steps thereafter on the specimens until the wait regions of all the specimens are calculated. When the wait regions of all the specimens are calculated, the processing of FIG. 16 is completed (in step S201).

When the wait region of a specimen is not yet calculated, the tracking unit 203 acquires (in step S202) a transfer route of the specimen from the transfer route information 291A (FIG. 8).

Thereafter (in step S203), the tracking unit 203 acquires from the received sensor values M271 the newest sensor value matching the specimen.

Subsequently (in step S204), the tracking unit 203 determines the wait region of the specimen and the queue order thereof by use of the newest sensor value acquired as above, adds the record to the wait region information D281, and registers the record.

At this time, the above wait region is determined to be: (1) a wait region corresponding to the location of one of the specimen detection sensors 304 which gives the newest sensor value, when the specimen is stopped by the stoppers 303 or the like and is in the state in which the specimen can be detected; and (2) a wait region to which the specimen goes next from the location of one of the specimen detection sensors 304 which gives the newest sensor value, which location is in the transfer route acquired from the transfer route information 291A, when the specimen is in the state in which the specimen is not yet detected.

Figure 17:
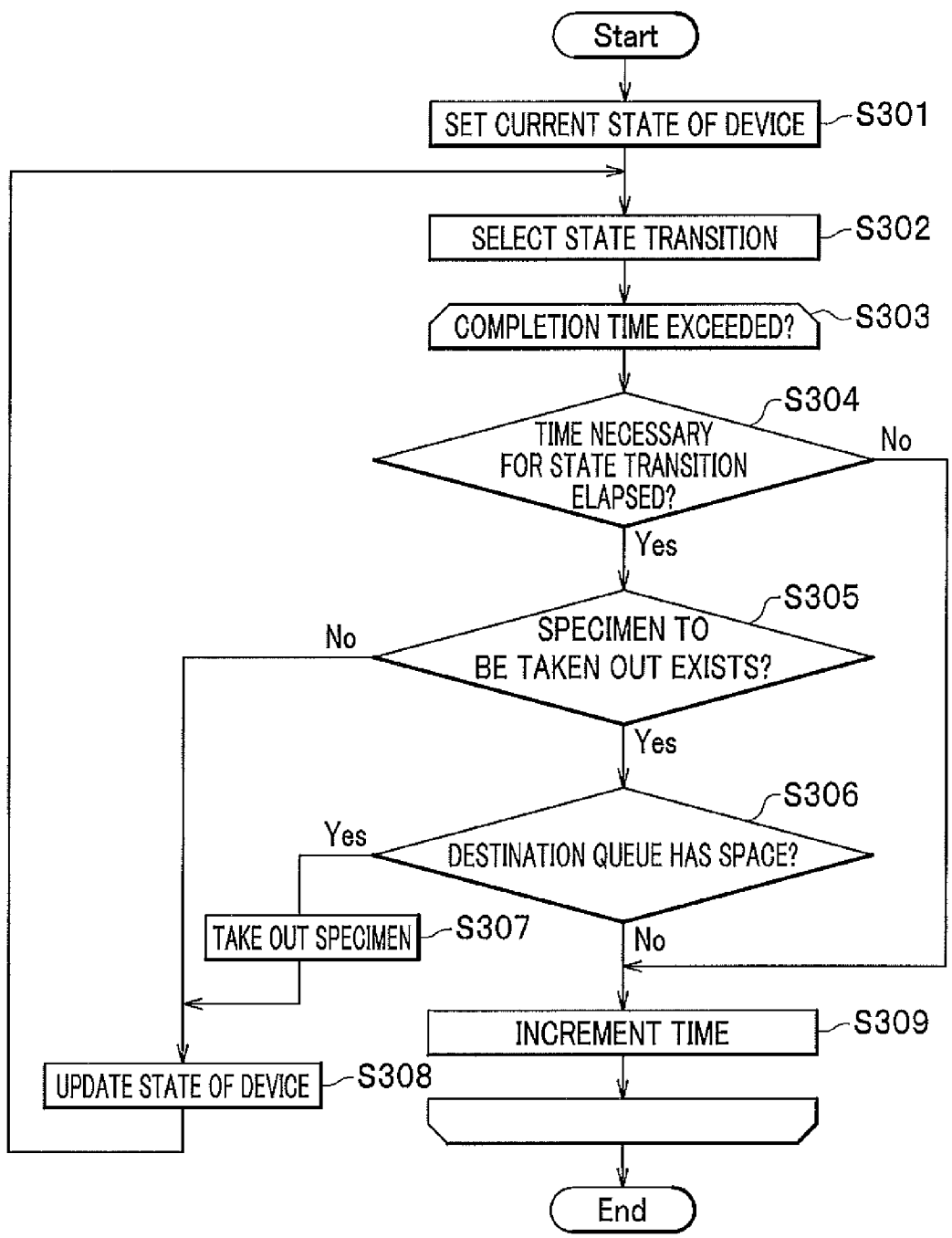
FIG. 17 is a flow chart of processing for calculation of estimated wait region information according to the first embodiment.

Next, processing (in step S106 of FIG. 15) for calculation of the congestion progress information is explained in detail with reference to FIG. 17. The above processing is performed for each model object in parallel.

First (in step S301), the simulation unit 205 sets the simulation time to the current time, and sets the current states of the devices in the model objects T400 (see FIG. 9).

Figure 15:
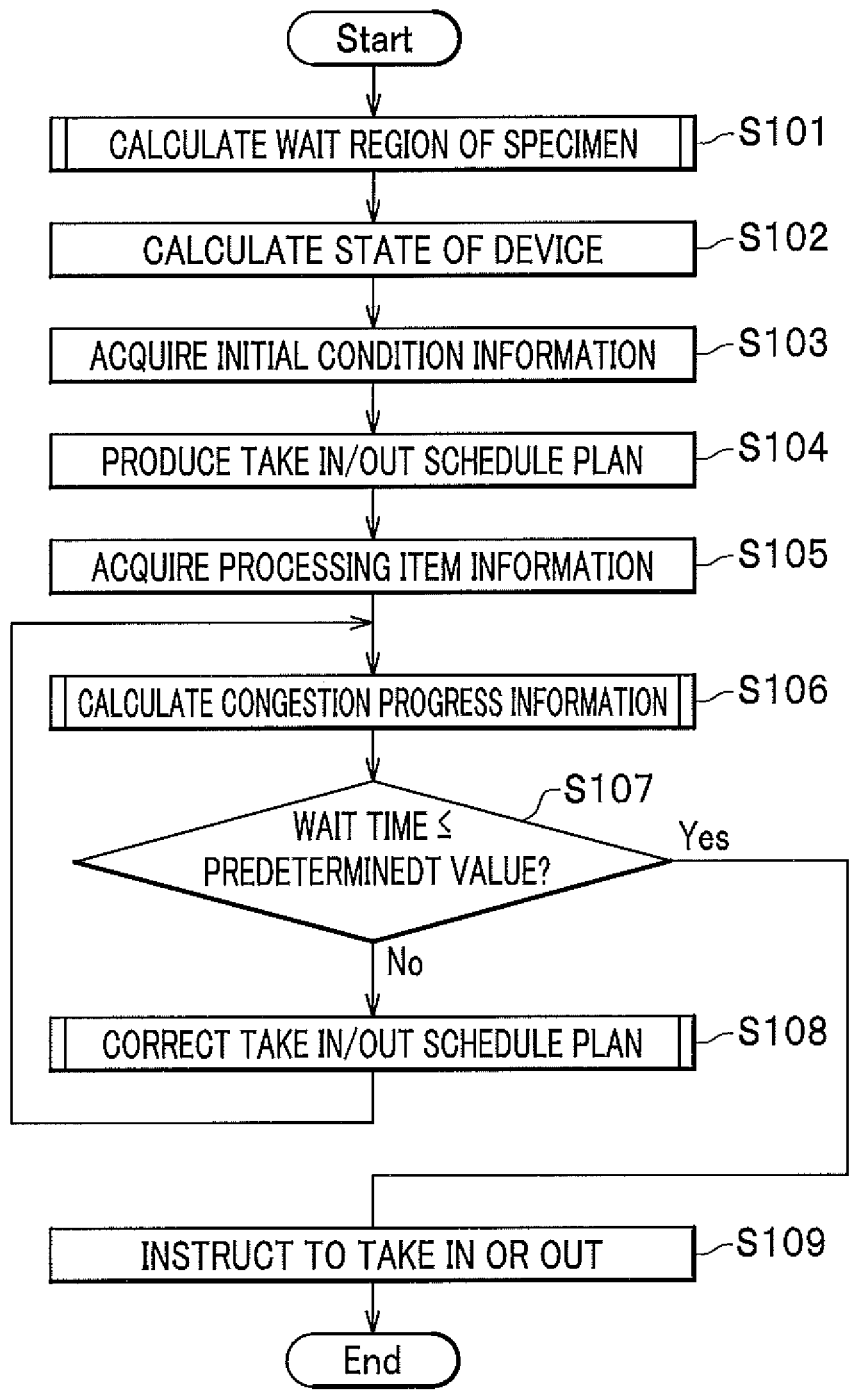
FIG. 15 is a flow chart illustrating an entire processing flow of the device management server according to the first embodiment.
Figure 16:
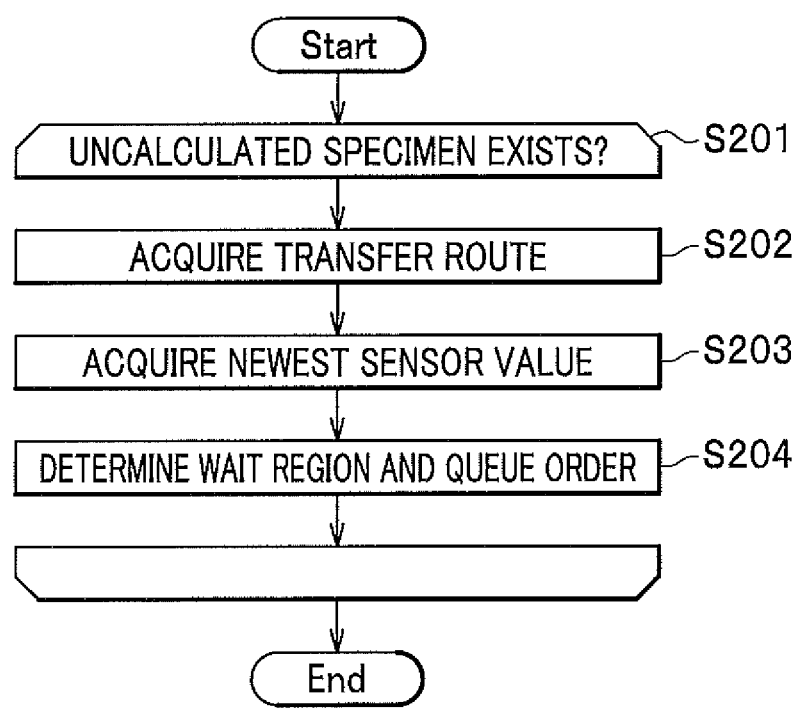
FIG. 16 is a flow chart of processing for calculation for the wait region for a specimen according to the first embodiment.

Specifically, the states of the devices calculated in step S102 in FIG. 15 are set as the current states of the model objects T400, and the state of wait of each specimen acquired from the wait region information D281 (see FIG. 14) is set in the queues in the model object T400.

In addition, a record indicating the wait time of each specimen at the current time is added to the congestion progress information D283, and the congestion progress information D283 is registered. At this time, the wait time of each specimen at the current time is calculated as the difference between the current time and the time of take-in which is detected by the specimen detection sensors 304.

After that (in step S302), the simulation unit 205 selects one of the state transitions defined in the state transition table T600 which satisfies the transition condition at the earliest time, by reference to the processing item information M274 for each specimen acquired in step S105 in FIG. 15.

When the simulation time does not exceed the completion time (which is ten minutes after the current time), the operation of the simulation unit 205 proceeds to step S304. When the simulation time exceeds the completion time, the processing of FIG. 17 is completed (step S303→End).

When the simulation time does not exceed the completion time, the simulation unit 205 determines (in step S304) whether or not the time needed for state transition satisfying the transition condition elapses, by reference to the state transition table T600.

When it is determined that the time needed for state transition elapses (i.e., when yes is determined), the operation goes to step S305. When the time needed for state transition does not elapse (i.e., when no is determined), the operation goes to step S309.

When the time needed for state transition elapses (i.e., when yes is determined in step S304), the simulation unit 205 determines (in step S305) whether or not a specimen to be taken out to the next wait region as a result of the state transition exists.

When it is determined that a specimen to be taken out exists (i.e., when yes is determined), the operation goes to step S306. When no specimen to be taken out exists (i.e., when no is determined), the operation goes to step S308.

That is, when a specimen to be taken out exists (i.e., when yes is determined in step S305), the simulation unit 205 determines (in step S306) whether or not an available space exists in the queue to which the specimen is to be taken out, by reference to the model object T400 for a device containing the queue which is the destination of the specimen to be taken out.

When it is determined that an available space exists in the queue which is the destination of the specimen to be taken out (i.e., when yes is determined), the operation goes to step S307. When no available space exists in the queue which is the destination of the specimen to be taken out (i.e., when no is determined), the operation goes to step S309.

When an available space exists in the queue which is the destination of the specimen to be taken out (i.e., when yes is determined in step S306), the simulation unit 205 takes out the specimen to the queue as the destination of the specimen to be taken out (in step S307).

Specifically, the simulation unit 205 makes a reservation for taking in a specimen which is to be taken out, into each queue as a destination of the specimen to be taken out, namely into the queue on which simulation is performed in parallel to the queue from which the specimen is taken out. In addition, the simulation unit 205 waits the time needed for the take-out, which is acquired on the basis of the corresponding processing time T604 in the state transition table T600. Thereafter, the simulation unit 205 deletes the data corresponding to the specimen from the queue from which the specimen is taken out. Further, the simulation unit 205 adds the time needed for the take-out to the wait time D2835, in the record of the congestion progress information D283, of each specimen remaining in the queue from which the specimen is to be taken out, and updates the time D2831 in the record of the congestion progress information D283.

The reservation for the take-in of the specimen is used as input data when the simulations for the other devices are performed, and is also used, when the available space in the queue as the destination is determined in step S306, for determining whether or not the space in the queue as the destination is exhausted by other specimens which are taken into the queue as the destination earlier than the concerned specimen.

After execution of step S307 is completed, or in the case where no specimen to be taken out exists (i.e., no is determined in step S305), the simulation unit 205 updates the state of the corresponding device by changing the current state T401 in the model object T400 to the state ID corresponding to the state after the transition according to the state transition table T600 (in step S308). Thereafter, the operation goes back to step S302, and the operations explained above are repeated.

When the elapsed time does not reach the time needed for the state transition (i.e., no is determined in step S304), or when no available space exists in the queue as the destination (i.e., no is determined in step S306), the simulation unit 205 increments the time so as to advance the simulation time by 100 milliseconds (in step S309). Thereafter, the operation goes back to step S303, and the operations explained above are repeated.

Figure 18:
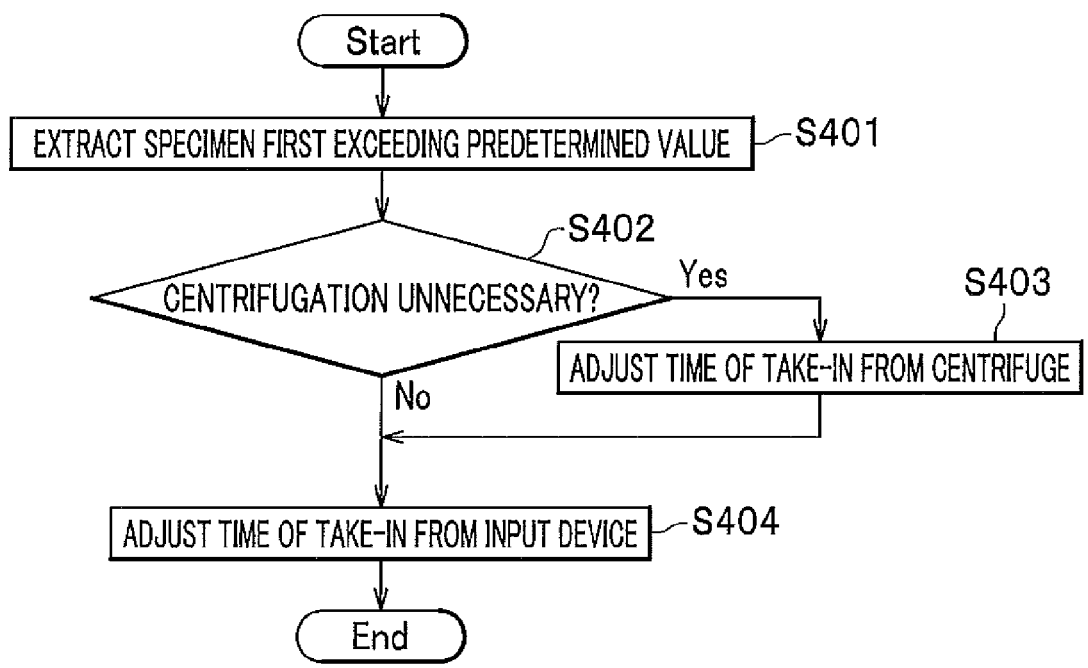
FIG. 18 is a flow chart of processing for correction of a take in/out schedule plan according to the first embodiment.

Next, processing (in step S108 in FIG. 15) for correcting the take in/out schedule plan D282 is explained in detail with reference to FIG. 18.

At first (in step S401), the take in/out scheduling unit 204 extracts a specimen of which the wait time D2835 registered in the congestion progress information D283 as a result of the simulation exceeds, at the earliest (first) time, the predetermined value (the allowable wait time M2735) for the corresponding wait region.

At this time, the time at which the predetermined value for the specimen being already taken out is exceeded is calculated by subtracting the difference between the wait time D2835 and the allowable wait time D2735 from the time D2831, and the time at which the predetermined value for the specimen being not yet taken out is exceeded is calculated by adding the allowable wait time D2735 to the time D2831 in the record for the last take-out registered in the congestion progress information D283.

Thereafter, the take in/out scheduling unit 204 determines whether or not centrifugation is unnecessary for the objective specimen (in step S402).

When it is determined that the objective specimen does not need centrifugation (i.e., when yes is determined), the operation goes to step S403. When the objective specimen needs centrifugation (i.e., when no is determined), the operation goes to step S404.

When the objective specimen does not need centrifugation (i.e., when yes is determined in step S402), the take in/out scheduling unit 204 adjusts the time of take-out from the centrifuge 102 (in step S403).

Specifically, the take in/out schedule plan D282 is corrected in such a manner that the time of take-out of each of other specimens using the same transfer path as the objective specimen in a time range around the time at which the objective specimen is transferred to the centrifuge 102 is delayed by two seconds.

When the objective specimen need centrifugation (i.e., when no is determined in step S402), or after the operation in step S403 is performed, the take in/out scheduling unit 204 adjusts the time of take-in from the input device 101 (in step S404).

Specifically, the take in/out schedule plan D282 is corrected in such a manner that the times at which a specimen two specimens preceding the objective specimen and the following specimens are taken in from the input device 101 are each delayed by two seconds.

For example, in the case where the centrifuge processes multiple normal specimens, and the processed normal specimens are taken out from the centrifuge at once, and congestion occurs in the device connected on the forward side of the centrifuge, and the wait times of urgent specimens being inputted after the congestion and not needing centrifugation exceed a predetermined value, the processing (in step S403) for adjusting the time of take-out from the centrifuge 102 suppresses take-out of normal specimens from the centrifuge and preferentially processes urgent specimens.

Here, an example of correction of a take-in schedule plan in the processing (in step S404) for adjusting the time of take-in from the input device 101 is explained with reference to FIG. 31 (a) to FIG. 31 (c).

For example, it is assumed that the wait time of a normal specimen S9 needing centrifugation exceeds the allowable wait time in the decapper 103 as a result of a simulation of operations performed when a specimen is inputted from an input device "Input 1" on the basis of the initial take-in schedule plan 3101 (FIG. 31 (a)).

In this case, the times of take-in of a specimen two specimens preceding the specimen S9 and the following specimens are delayed.

At first, a first correction is made. By the first correction, the time of take-in of each of the specimens S7, S8, and S9 is delayed by two seconds (in accordance with the take-in schedule plan 3102 according to the first correction (FIG. 31 (b)).

When the wait time of the specimen S9 exceeds the allowable wait time again even after the first correction made as above, a second correction is made.

After the second correction, the time of take-in of each of the specimens S7, S8, and S9 is delayed by four seconds from the original time of take-in (in accordance with the take-in schedule plan 3103 according to the second correction (FIG. 31 (c)).

When the wait time of every specimen in every wait region is brought equal to or smaller than the allowable wait time by one or more corrections of the take-in schedule plan, the correction of the take in/out schedule plan D282 is completed.

Further, in the second and following corrections, the number of preceding specimens of which the times of take-in are delayed may be successively increased.

In the present embodiment, the time of take-out or take-in is delayed by two seconds in each correction. However, the amount of the increase in the delay may be greater or smaller than two seconds according to the processing performance of the device management server 108.

In addition, in the present embodiment, the number of preceding specimens of which the times of take-in are delayed is two. However, the number of preceding specimens of which the times of take-in are delayed may be greater or smaller than two.

Further, in the case where the time of take-out from the centrifuge 102 is adjusted, the adjustment of the time of take-in from the input device 101 may be dispensed with.

Furthermore, although the processing in the present embodiment is performed in a heuristic manner, it is possible to define as operators operations of changing the order and times of take-in and take-out, and also use an optimization method such as the Monte Carlo method.

Even in the above case, it is possible to quickly make the correction by intensively adding corrections in a time range around a time of take-in or take-out of a specimen of which the wait occurs.

Moreover, in the present embodiment, the correction is performed for a single specimen of which wait time exceeds the allowable wait time at the earliest time. However, corrections for multiple specimens the wait times of which exceed the allowable wait time may be made at once.

In addition, in the present embodiment, the schedule plan is corrected by performing the simulation for the ten-minute period starting from the current time, at intervals of 100 milliseconds. However, the schedule plan may be corrected by detecting occurrence of congestion on the basis of the number of specimens in the wait region and the position of the wait region.

Next, a method for registering the scheduling parameter table T800 (see FIG. 12) is explained with reference to FIGS. 19 and 20.

Figure 19:
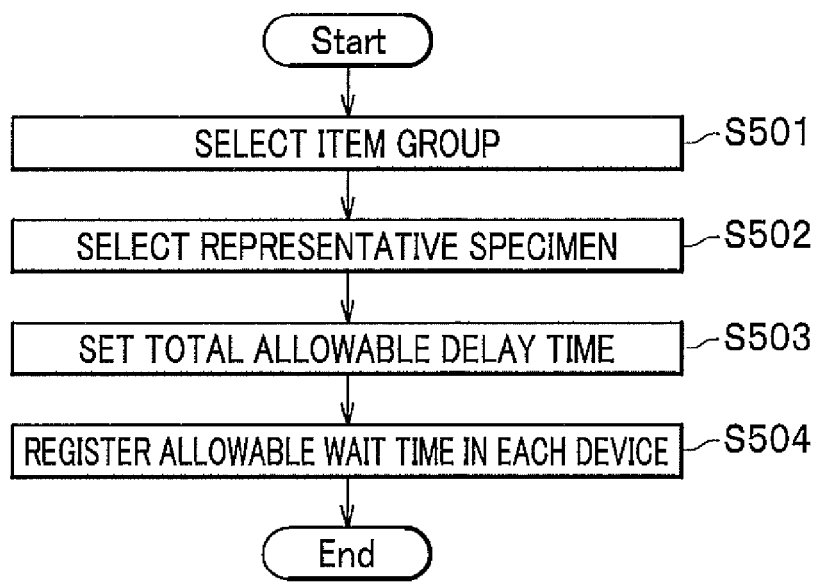
FIG. 19 is a flow chart of processing for registration of scheduling parameters according to the first embodiment.

FIG. 19 is a flow chart indicating an example of processing for registering the scheduling parameter table T800, and FIG. 20 is a flow chart indicating an example of display of a screen for registering scheduling parameters, which is used in the processing for registering the scheduling parameter table T800.

Input into and output from the screen for registering scheduling parameters are controlled by the operations management unit 208 in the operations terminal 110.

At first, a person who performs operation for registration such as a laboratory technician chooses an arbitrary item group from item groups registered in advance by using an item-group combo box G101 (in step S501).

At this time, a transfer route of a specimen corresponding to the chosen item group is graphically displayed on a flow view G102. Therefore, the person performing the operation for registration chooses a representative specimen for which parameter is to be registered, from among transferred specimens (primary specimens and aliquoted secondary specimens), by confirming the transfer route displayed on the flow view G102 and using a representative-specimen combo box G103 (in step S502).

In response to the above choice of the representative specimen, an estimated time of the TAT for the case where processing is performed in the shortest time is displayed in a shortest-processing-time box G104.

The above estimated time is a result of a simulation performed in advance on the assumption that only one specimen in the corresponding item group is processed in the simulation.

After that (in step S503), a maximum delay time which is allowable when the chosen representative specimen is an urgent specimen is set by using an allowable-delay-time combo box G105.

Finally, when the person performing the operation for registration presses on the OK button G106 (by clicking the OK button G106 with the mouse), the operations management unit 208 registers an allowable wait time T803 in each wait region in each device in a record for the wait region in the device in the scheduling parameter table T800 (in step S504), where the allowable wait time T803 in each wait region in each device is the sum of the wait time (T1) in the wait region in the device which occurs when the device operates with the maximum processing performance without wait and the quotient (T2) obtained by dividing of the maximum delay time divided by the number of wait regions through which the specimen is to be transferred.

In addition, the person performing the operation for registration can quit the operation for registration by pressing on the Cancel button G107.

As explained above, in the automatic analysis system according to the first embodiment, the wait times of all specimens as urgent specimens and normal specimens in each wait region can be suppressed to or below a predetermined value, so that the TATs of the urgent specimens can always be brought within a target time range.

<Second Embodiment>

In the second embodiment, an example of an automatic analysis system having a device configuration in which a transfer route is halfway divided into two.

<System Configuration>

Figure 21:
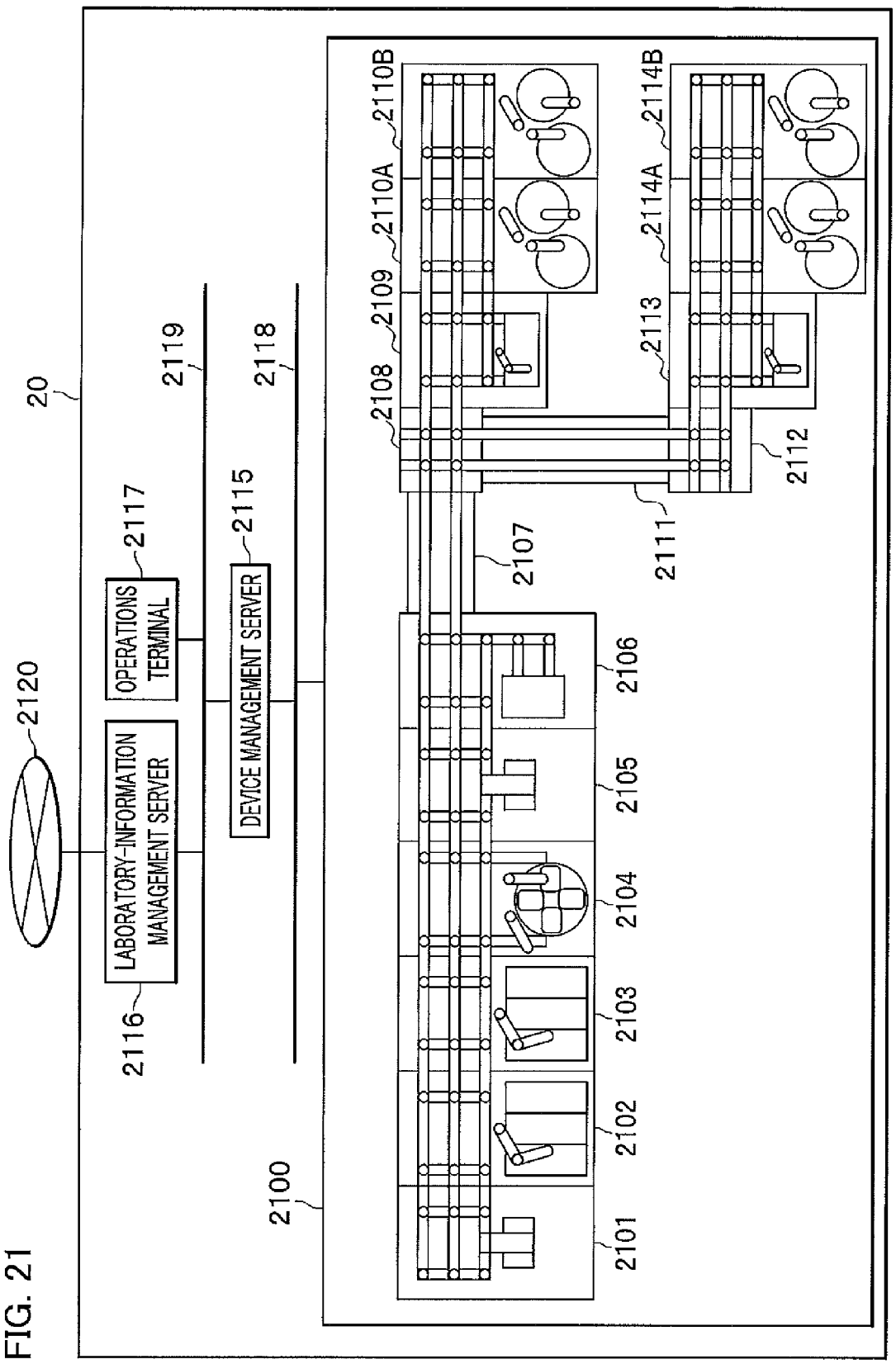
FIG. 21 is a system configuration diagram illustrating an example of an automatic analysis system according to the second embodiment.

FIG. 21 is a system configuration diagram of the automatic analysis system according to the second embodiment.

As illustrated in FIG. 21, the automatic analysis system 20 includes a testing device group 2100, a device management server 2115, a laboratory-information management server 2116, and an operations terminal 2117.

Each device in the testing device group 2100 and the device management server 2115 are communicably connected through a device information network 2118 such as a LAN. Similarly, the device management server 2115, the laboratory-information management server 2116, and the operations terminal 2117 are communicably connected through a test-information network 2119 such as a LAN.

In addition, the laboratory-information management server 2116 is connected through a hospital network 2120 to another system in a hospital such as an electronic medical record system.

The testing device group 2100 includes a recapper 2101, a storing device 2102, an input device 2103, a centrifuge 2104, a decapper 2105, an aliquoter 2106, linear conveyors 2107 and 2111, redirectors 2108 and 2112, buffer devices 2109 and 2113 capable of changing the order of take-out of specimens, colorimetric analyzers 2110 (A, B), and immunoassay devices 2114 (A, B), which are arranged as illustrated in FIG. 21.

<Function Constitution>

Figure 22:
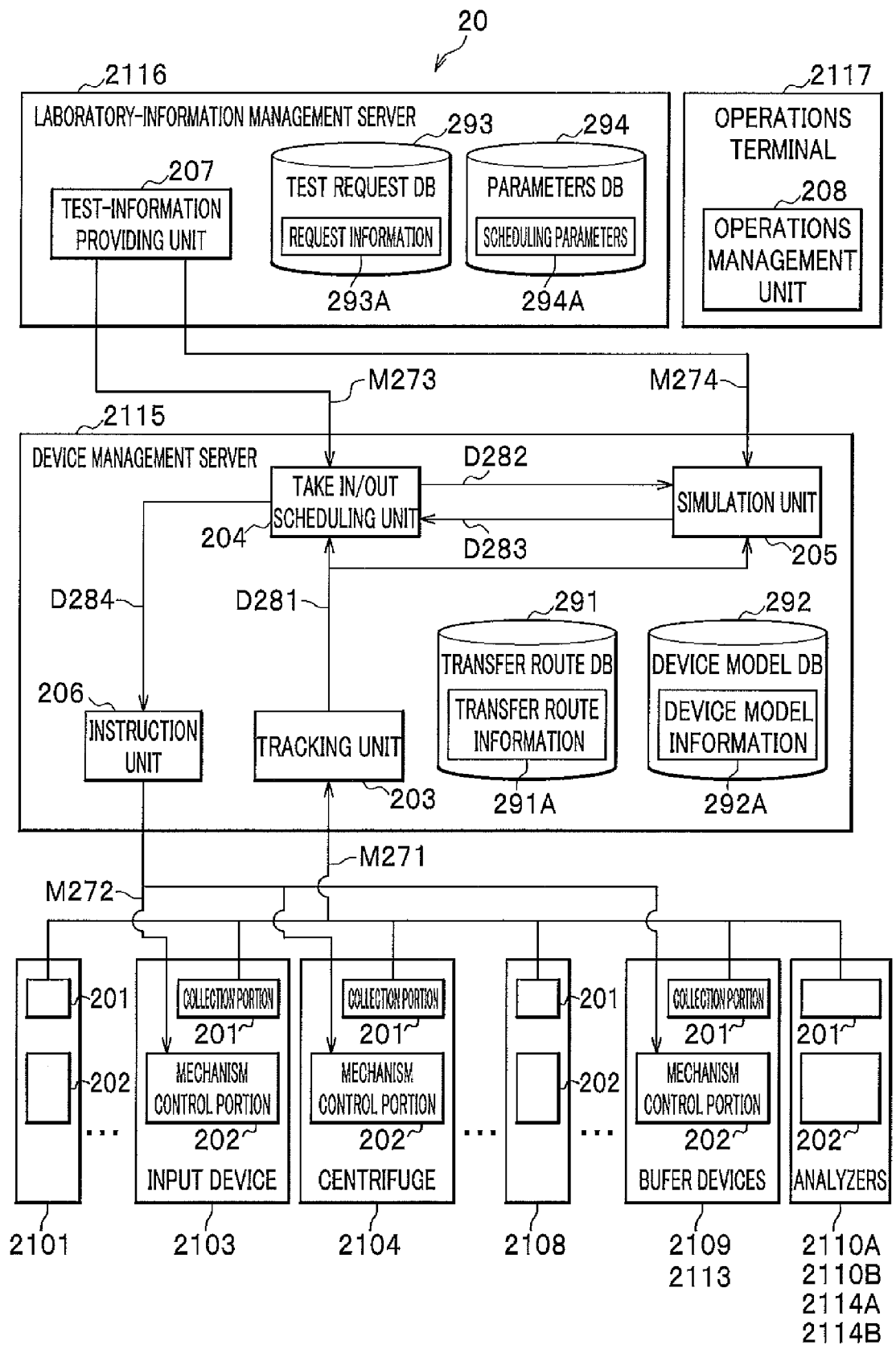
FIG. 22 is an explanatory diagram indicating functions and operations of the automatic analysis system according to the second embodiment.

FIG. 22 is an explanatory diagram indicating functions and operations of the automatic analysis system 20 according to the second embodiment.

Firstly, the functions and operations of the automatic analysis system 20 are explained with reference to FIG. 22.

Each device as a constituent of the testing device group 2100 has a collection portion 201 and a mechanism control portion 202.

The device management server 2115 includes a tracking unit 203, a take in/out scheduling unit 204, a simulation unit 205, an instruction unit 206, a transfer route DB 291 and a device model DB 292.

The laboratory-information management server 2116 includes a test-information providing unit 207, a test request DB 293, and a parameters DB 294.

In addition, the operations terminal 2117 includes an operations management unit 208.

<Outline of Operations>

Next, an outline of operations of the automatic analysis system 20 is explained with reference to FIG. 22.

In the following explanations, the following first and second cases are considered. In the first case, a specimen requiring a high aliquot ratio is inputted before input of an urgent specimen, so that the processing capacity of the aliquoter 2106 is exceeded, and congestion occurs on the upstream side of the aliquoter 2106. In the second case, the "return movement", for example, for examining a specimen in the colorimetric analyzer 2110 (A, B) and thereafter examining the specimen in the immunoassay device 2114 (A, B), frequently occur, so that the processing capacity of the redirector 2108 is exceeded, and congestion occurs on the upstream and downstream sides of the redirector 2108.

The collection portion 201 in each device as a constituent of the testing device group 2100 transmits the sensor value M271 indicating the state of specimen detection in each of parts of the device to the tracking unit 203 in the device management server 2115.

The tracking unit 203 in the device management server 2115 determines the current position of each specimen and calculates the state of existence of one or more specimens (the wait region information D281) in each region in which a specimen can stay in each device, by using the sensor value M271 from each device and the transfer route determined by the test item of each specimen which is instructed by the take in/out instruction M272 to take in or out.

Then, the take in/out scheduling unit 204 in the device management server 2115 generates an initial take in/out schedule plan D282 in which priority is assigned to urgent specimens, on the basis of the initial condition information M273 and the wait region information D281.

Subsequently, the simulation unit 205 in the device management server 2115 calculates estimated amounts of the wait times in each wait region in a period until a predetermined time elapses (the congestion progress information D283) in the case where specimens are taken in and out in accordance with the generated take in/out schedule plan D282, by a simulation based on the processing item information M274, the transfer route information 291A, and device model information 292B.

Then, the take in/out scheduling unit 204 repeats a correction of the take in/out schedule plan D282 and a simulation as above so as to bring the estimated amounts of the wait times equal to or below a predetermined value given by the initial condition information M273, where the timings and order of take-in and take-out are changed in the correction of the take in/out schedule plan D282. Thus, the take in/out schedule D284 is generated in the end.

Finally, the instruction unit 206 transmits the take in/out instruction M272 to the mechanism control portions 202 in the input device 2103, the centrifuge 2104, and the buffer devices 2109 and 2113 in accordance with the produced take in/out schedule D284.

The above operations of the automatic analysis system 20 can suppress the wait times in each wait region in the system to a value equal to or below the predetermined value, and can therefore bring the TATs of the urgent specimens within a predetermined time range.

<Transfer Mechanism>

The structures of the internal mechanisms of the devices other than redirectors 2108 and 2112 are similar to the internal mechanisms of the devices explained in the first embodiment.

In the second embodiment, it is assumed that the input device 2103 can take in specimens at any timings in an any order by using an XYZ table and a robot arm, and can recognize the identification information for the specimens attached to the specimens or trays.

In addition, it is also assumed that specimens can also be taken out from the centrifuge 2104 and the buffer devices 2109 and 2113 at any timings in an any order by using the XYZ table and the robot arm.

Figure 23:
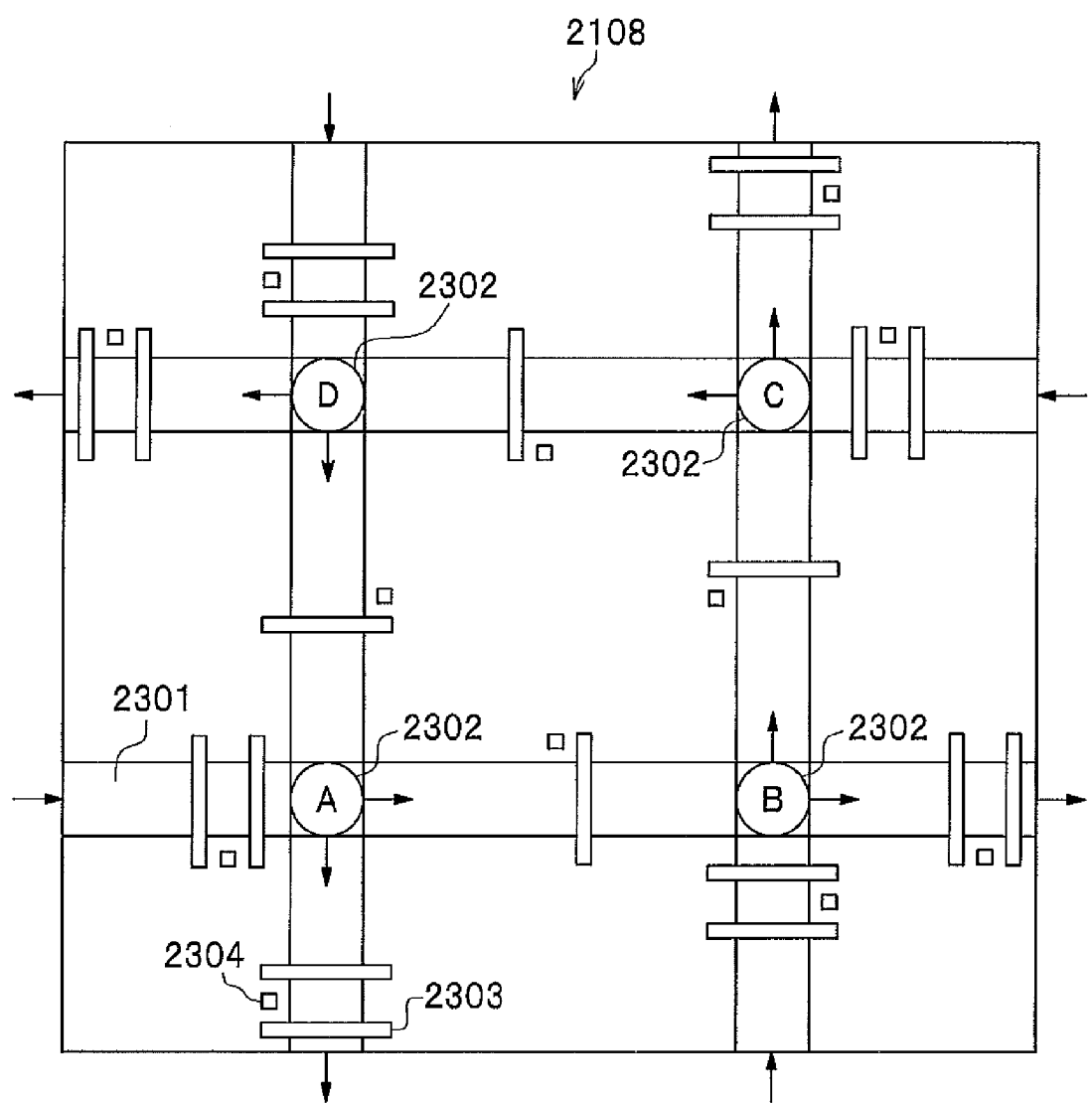
FIG. 23 is an explanatory diagram illustrating an example of the structure of the internal mechanism of a redirector according to the second embodiment.

FIG. 23 illustrates an example of a structure of an internal mechanism of the redirector 2108.

The transfer mechanisms in the redirectors 2108 and 2112 are explained in detail below with reference to FIG. 23.

The redirector 2108 illustrated in FIG. 23 includes conveyor lines 2301, redirection mechanisms 2302, stoppers 2303, and specimen detection sensors 2304.

The function of each of the above mechanisms in the redirector 2108 is similar to the function of the corresponding mechanism in the first embodiment explained before.

Hereinafter, regions as the redirection mechanisms 2302 which need exclusive control are referred to as common portions.

The operations of the redirector 2108 in the present embodiment are briefly explained below.

While the transfers of specimens in the devices other than the redirector 2108 are asynchronously controlled by each stopper, specimens in the redirector 2108 are transferred from one queue to another queue in each control cycle (e.g., every second).

At this time, multiple queues are concurrently processed unless specimens transferred to or from the multiple queues go through the same common portion.

Figure 24:
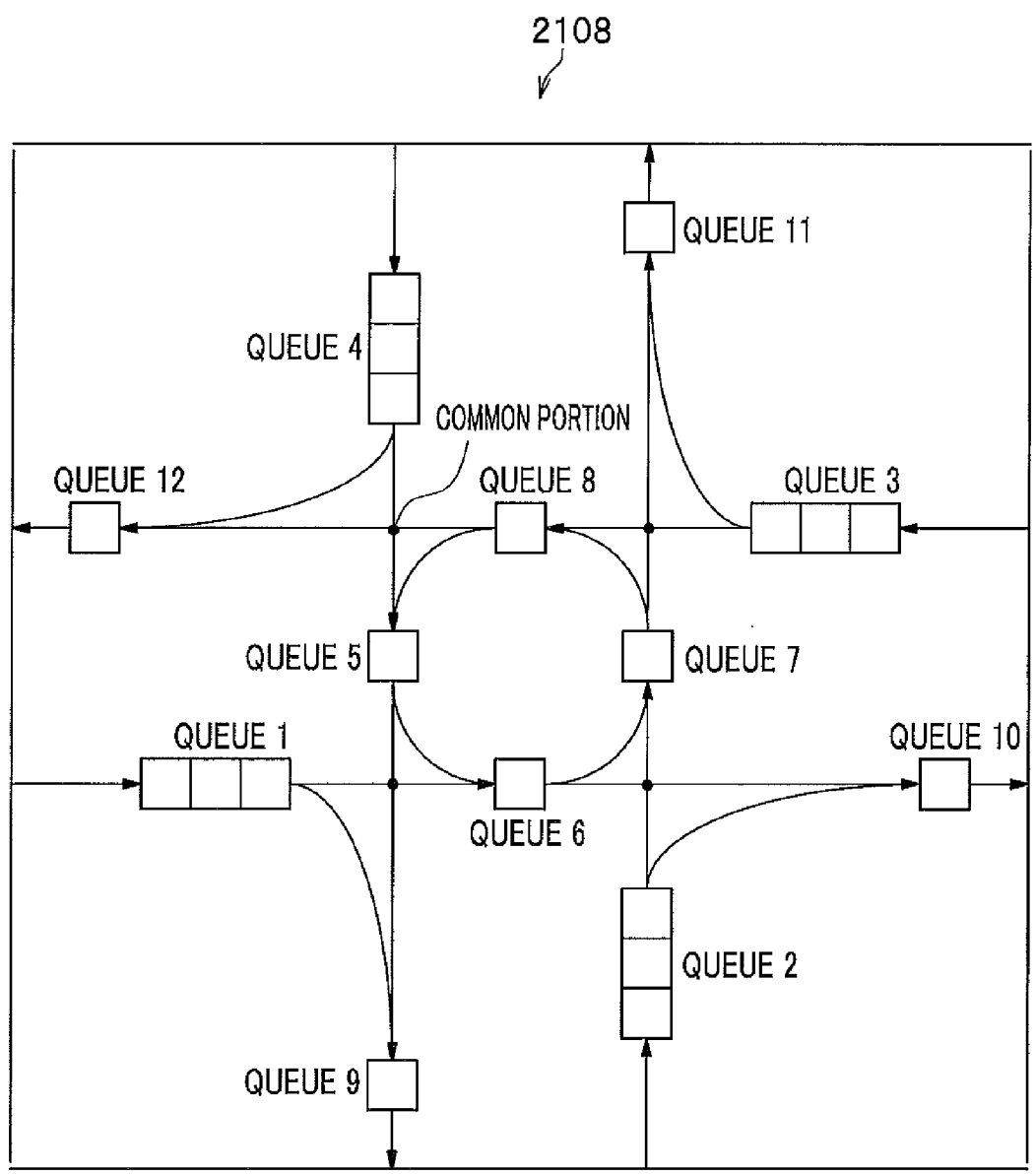
FIG. 24 is a diagram representing by a queue model an example of the structure of the internal mechanism of the redirector according to the second embodiment.

For example, in FIG. 24 (which represents by a queue model the structure of the internal mechanism of the redirector illustrated in FIG. 23), the transfer from the queue 4 to the queue 12 and the transfer from the queue 6 to the queue 10 can be performed in the same control cycle.

On the other hand, the transfer from the queue 4 to the queue 12 and the transfer from the queue 8 to the queue 5 cannot be performed in the same control cycle, because both of the transfers use the common portion illustrated in the upper left part of FIG. 24.

Next, the characteristics of the processing performance of the redirection mechanisms 2302 are explained.

In the case where successive transfer of specimens from the queue 1 to the queue 10 and successive transfer of specimens from the queue 3 to the queue 12 are performed in the same time zone, the specimens transferred from the queue 1 to the queue 10 pass through common portions different from the common portions through which the specimens transferred from the queue 3 to the queue 12 pass. Therefore, all of the specimens from the queue 1 to the queue 10 and the specimens from the queue 3 to the queue 12 can be transferred with the maximum performance.

On the other hand, in the case where successive transfer of specimens from the queue 1 to the queue 10 and successive transfer of specimens from the queue 3 to the queue 9 are performed in the same time zone, the specimens transferred from the queue 1 to the queue 6 and the specimens transferred from the queue 5 to the queue 9 use the same common portion illustrated in the lower left part of FIG. 24.

For example, it is possible to control the queues in such a manner that the queue 5 always precedes the queue 1 in transfer of specimens, and specimens are transferred from the queue 5 to the queue 9 until no specimen is left in the queue 5.

Alternatively, it is possible to control the queues in such a manner that the queue 1 always precedes the queue 5 in transfer of specimens, and specimens are transferred from the queue 1 to the queue 6 until no specimen is left in the queue 1.

Therefore, in the redirector 2108, (1) the performance of transfer of specimens is lowered when the same common portion is concurrently used in multiple transfer routes compared with when no common portion is concurrently used in multiple transfer routes.

In addition, (2) the balance in the transfer performance between different transfer directions in the redirector 2108 can be adjusted by controlling the priorities assigned to queues from which the transfers use the same common portion.

<Hardware Construction>

The hardware construction of each device in the testing device group 2100 is similar to the hardware construction of each device in the testing device group 100 explained in the first embodiment.

The hardware construction of the device management server 2115 is similar to the hardware construction in the device management server 108 which is explained in the first embodiment.

The hardware construction of the laboratory-information management server 2116 is similar to the hardware construction of the laboratory-information management server 109 explained in the first embodiment.

The hardware construction of the operations terminal 2117 is similar to the hardware construction of the operations terminal 110 explained in the first embodiment.

<Correspondence Between Functions and Hardware>

The correspondences between the functions and the hardware in each device in the automatic analysis system 20 are similar to the first embodiment except that the device model information 292B replaces the device model information 292A.

<Information Structure>

The information structure of the automatic analysis system 20 are similar to the first embodiment except that the device model information 292B replaces the device model information 292A.

Therefore, only the device model information 292B in the automatic analysis system 20 is explained in detail below with reference to FIGS. 9, 23, 24, and 25.

(Device Model Information)

Figure 25:
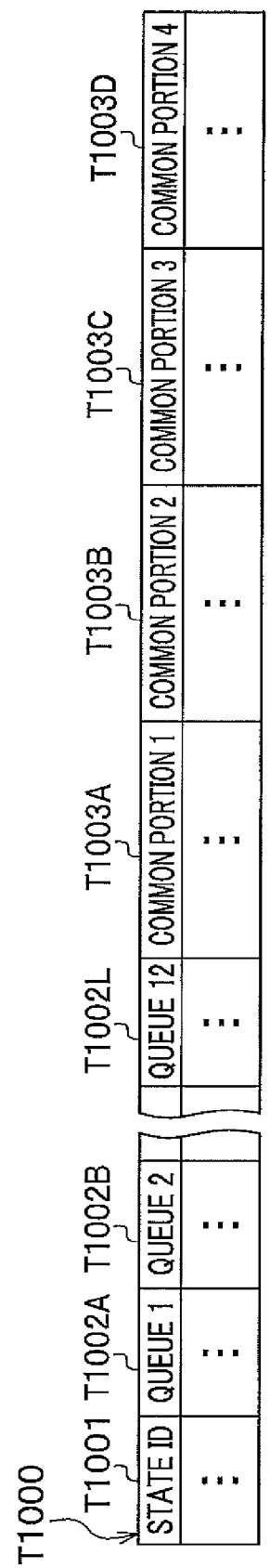
FIG. 25 is a diagram illustrating an example of a data structure of a state definition table for the redirector, which is added to the device model information according to the second embodiment.

The device model information 292B is information for use by the simulation unit 205 in execution of the simulation, and includes the model objects T400, the state definition table T500, the state transition table T600, and the connection definition table T900 (which are illustrated as examples in FIG. 9) and the state definition table T1000 for redirectors (illustrated as an example in FIG. 25).

The model objects T400, the state definition table T500, the state transition table T600, and the connection definition table T900 are similar to those explained in the first embodiment.

In addition, the take in/out schedule D284 (FIG. 14) has the same structure as the first embodiment.

However, the indication values D2844 for the redirectors 2108 and 2112 each indicate the direction in which specimens are to be preferentially taken in, instead of indicating whether to take in or take out.

Specifically, the indication values D2844 for the redirectors 2108 and 2112 are each one of the integers (0, 1, 2, 3, and 4) for respectively indicating "No Priority", "Left First", "Down First", "Right First", and "Up First", which are listed as preferential take-in directions in the preferred-queue determination rule table T2000 (FIG. 28) (which is explained later).

The state definition table T1000 for redirectors illustrated in FIG. 25 defines the state of the redirector 2108, and includes as attributes the state ID (T1001), the queues 1 to 12 (T1002A to T1002L), and the common portions 1 to 4 (T1003A to T1003D).

The common portions indicate the states of use of regions which need exclusive control as the redirection mechanisms 2302 (A to D) in FIG. 23.

The reason for adding the states of use to the state definition table for the redirector 2108, but not to the state definition table for the other devices, is to prescribe the exclusive control operation mentioned before.

Since the transfer directions and transfer times of specimens are set for each state discriminately defined in the state definition table T1000 for redirectors, more precise simulation is enabled.

<Processing Flow>

Next, an outline of processing for controlling the order and timings of take-in and take-out of specimens in each device in order to prevent congestion with the specimens in the device is explained.

Each device in the present embodiment is assumed to process specimens taken in, in accordance with the processing item IDs (see T102 in FIG. 8), and take out the processed specimens.

The basic flow of processing in the second embodiment is similar to flow of processing in the first embodiment except the concurrent use of the state definition table T500 and the state definition table T1000 for redirectors and the processing for correction of the take in/out schedule plan.

Figure 26:
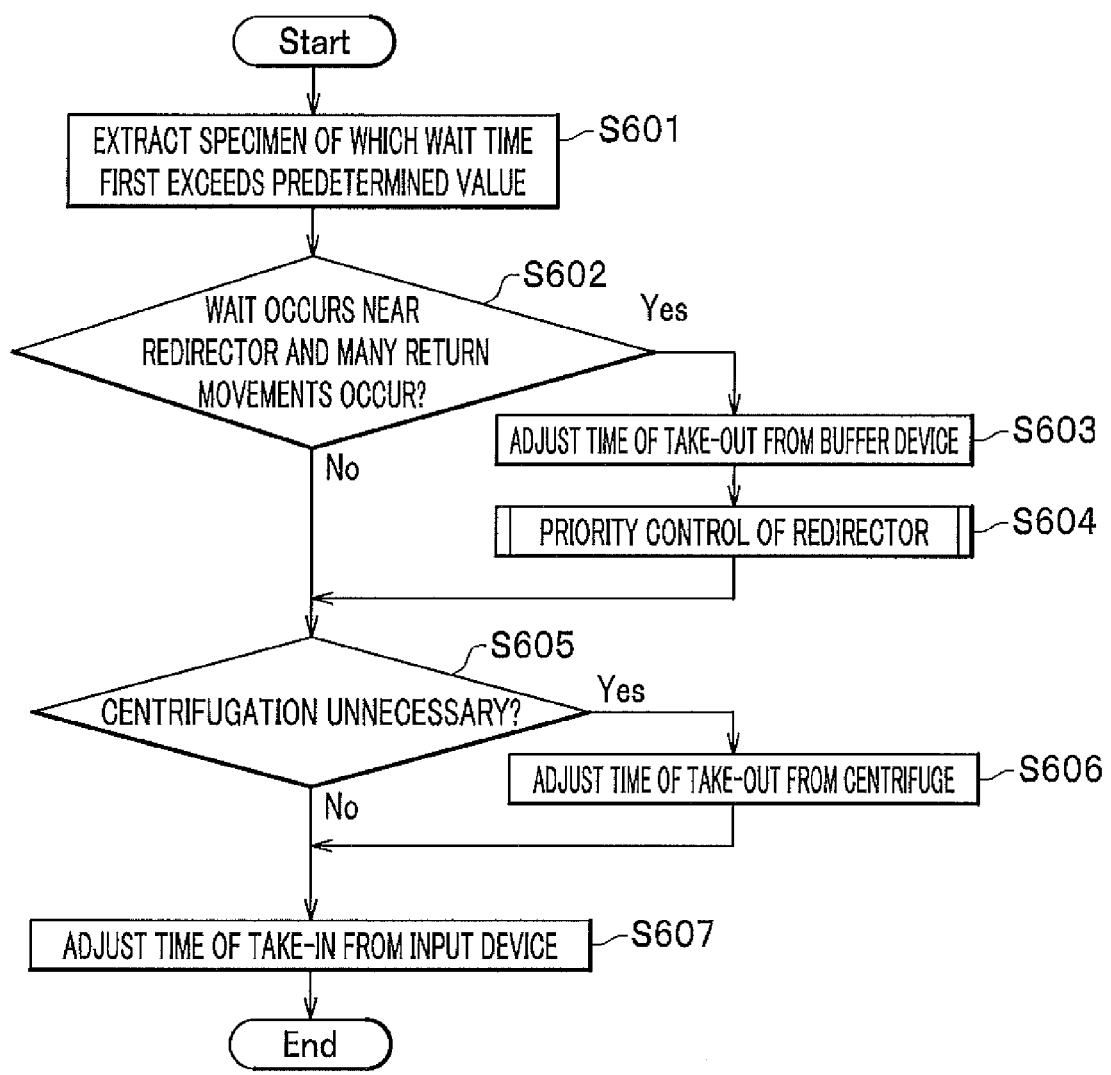
FIG. 26 is a flow chart of processing for correction of a take in/out schedule plan according to the second embodiment.

Hereinbelow, processing (in step S108 in FIG. 15) for correction of the take in/out schedule plan D282 in the second embodiment is explained in detail with reference to FIG. 26.

At first (in step S601), the take in/out scheduling unit 204 extracts a specimen of which the wait time D2835 registered in the congestion progress information D283 as a result of a simulation exceeds the predetermined value (the allowable wait time M2735) in the corresponding wait region at the earliest time.

At this time, the manner of calculation of the time at which the predetermined value is exceeded is similar to step S401 (in FIG. 18), which is explained before.

After that (in step S602), the take in/out scheduling unit 204 determines, by reference to the congestion progress information D283, whether or not a wait occurs around the redirector 2108 or 2112 and many return movements in which specimens go through an identical wait region multiple times occur.

When it is determined that a wait occurs around the redirector 2108 or 2112 and many return movements occur (i.e., when yes is determined), the operation goes to step S603. Otherwise (i.e., when no is determined), the operation goes to step S605.

When a wait occurs around the redirector 2108 or 2112 and many return movements occur (i.e., when yes is determined in step S602), the take in/out scheduling unit 204 adjusts the times of take-out from the buffer devices 2109 and 2113 (in step S603).

Specifically, the take in/out scheduling unit 204 corrects the take in/out schedule plan D282 so as to delay by two seconds the times of take-out of normal specimens in the buffer devices 2109 and 2113, in the time range around the time at which the objective specimen is taken out from the buffer device 2109 or 2113.

In the above operation, when 30% or more of specimens taken into the redirectors 2108 and 2112 make a return movement, the take in/out scheduling unit 204 determines that many return movements occur.

Although the criterion for the above determination is 30% in the present embodiment, the criterion may be greater or smaller than 30% according to the system configuration or the use of the system.

Then, the take in/out scheduling unit 204 performs priority control of the redirectors 2108 and 2112 (in step S604).

Specifically, the take in/out scheduling unit 204 controls the redirectors 2108 and 2112 so as to preferentially transfer specimens from a wait region which is most congested with specimens (i.e., a wait region in which the sum of wait times of specimens is greatest) in the devices adjacent to the redirectors 2108 and 2112 in respective directions (e.g., the linear conveyors 2107 and 2111 and the buffer device 2109 adjacent to the redirector 2108).

Although the priority control according to the present embodiment is performed on the adjacent devices, the priority control may be performed on the aliquoter 2106 and the buffer device 2113, instead of the linear conveyors 2107 and 2111 which do not directly contribute to the congestion of specimens.

In the case where no wait occurs around the redirectors 2108 and 2112, or many return movements do not occur (i.e., no is determined in step S602), or after execution of step S604, the take in/out scheduling unit 204 determines whether or not centrifugation of the objective specimen is unnecessary (in step S605).

When it is determined that centrifugation of the objective specimen is unnecessary (i.e., when yes is determined), the operation goes to step S606. Otherwise (i.e., when no is determined), the operation goes to step S607.

When centrifugation of the objective specimen is unnecessary (i.e., when yes is determined in step S605), the take in/out scheduling unit 204 adjusts the times of take-out from the centrifuge 2104 (in step S606).

Specifically, the take in/out scheduling unit 204 corrects the take in/out schedule plan D282 so as to delay by two seconds the times of take-out, from the centrifuge 2104, of normal specimens other than the objective specimen which use the same transfer path as the objective specimen in the time range around the time of transfer of the objective specimen in the centrifuge 2104.

When centrifugation of the objective specimen is necessary (i.e., when no is determined in step S605), or after execution of step S606, the take in/out scheduling unit 204 adjusts the times of take-in from the input device 2103 (in step S607).

Specifically, the take in/out schedule plan D282 is corrected in such a manner that the times at which a specimen which precedes the objective specimen by two specimens and the following specimens are taken in are each delayed by two seconds.

For example, in the case where normal specimens are processed in an analyzer and the processed specimens are taken out, and the difference in the transfer route between urgent specimens being transferred toward the analyzer and the normal specimens being returned from the analyzer causes a conflict and a congestion around a redirector, and makes the wait times of the urgent specimens transferred toward the analyzer exceed a predetermined value, the processing (in step S603) for adjusting the times of take-out from the buffer devices and the processing (in step S604) for priority control of the redirectors guarantee the TAT and operate the system with high efficiency by suppressing take-out of specimens from the analyzer and preferentially processing urgent specimens.

Hereinbelow, the processing (in step S604 in FIG. 26) for priority control of the redirectors is explained in detail.

Before the explanation, a set of queues on the source side from which specimens can be transferred, by one operation, to each queue (e.g., each of the queues 9, 10, 11, and 12 in FIG. 24) corresponding to an outlet of a redirector is defined as a "block".

In the example of FIG. 24, it is assumed that the block 1 is constituted by the queues 1 and 5, the block 2 is constituted by the queues 2 and 6, the block 3 is constituted by the queues 3 and 7, and the block 4 is constituted by the queues 4 and 8.

Next, a flow of the processing for priority control of the redirectors is explained in detail with reference to FIG. 27.

At first (in step S701), one of the directions from the adjacent devices including a specimen which will have to wait the longest time (which is referred to as the maximum-wait direction) and the longest wait time per se (which is referred to as the maximum wait time) are obtained by calculation by reference to the congestion progress information D283.

Thereafter, the priority order of the queues is set on the basis of the preferred-queue determination rule table (T2000) illustrated in FIG. 28 (in step S702).

Specifically, when the maximum wait time does not exceed the predetermined value for each wait region, the order indicated as "No Priority" is set. In this case, the queue 5 precedes the queue 1 in the block, the queue 6 precedes the queue 2 in the block 2, the queue 7 precedes the queue 3 in the block 3, and the queue 8 precedes the queue 4 in the block 4.

When the maximum wait time exceeds the predetermined value for each wait region, the maximum-wait direction is determined to be the preferred take-in direction.

For example, when the preferred take-in direction is determined to be "Right First", the priority order is set in such a manner that the queue 5 precedes the queue 1 in the block, the queue 6 precedes the queue 2 in the block 2, the queue 3 precedes the queue 7 in the block 3, and the queue 8 precedes the queue 4 in the block 4.

After that (in step S703), a transfer control schedule for each queue is produced by calling a SolveBlock process with an identifier (as an argument) indicating each block, where the processing is successively performed, by reference to the congestion progress information D283, for the respective blocks in decreasing order of the wait time which a specimen included in the direction corresponding to each block from the adjacent devices will have to wait. The SolveBlock process is explained later.

In the following explanations, the queue determined to be preferred in each block corresponding to the block identifier is referred to as a high priority queue, and the other queues are referred to as low priority queues.

Figure 29:
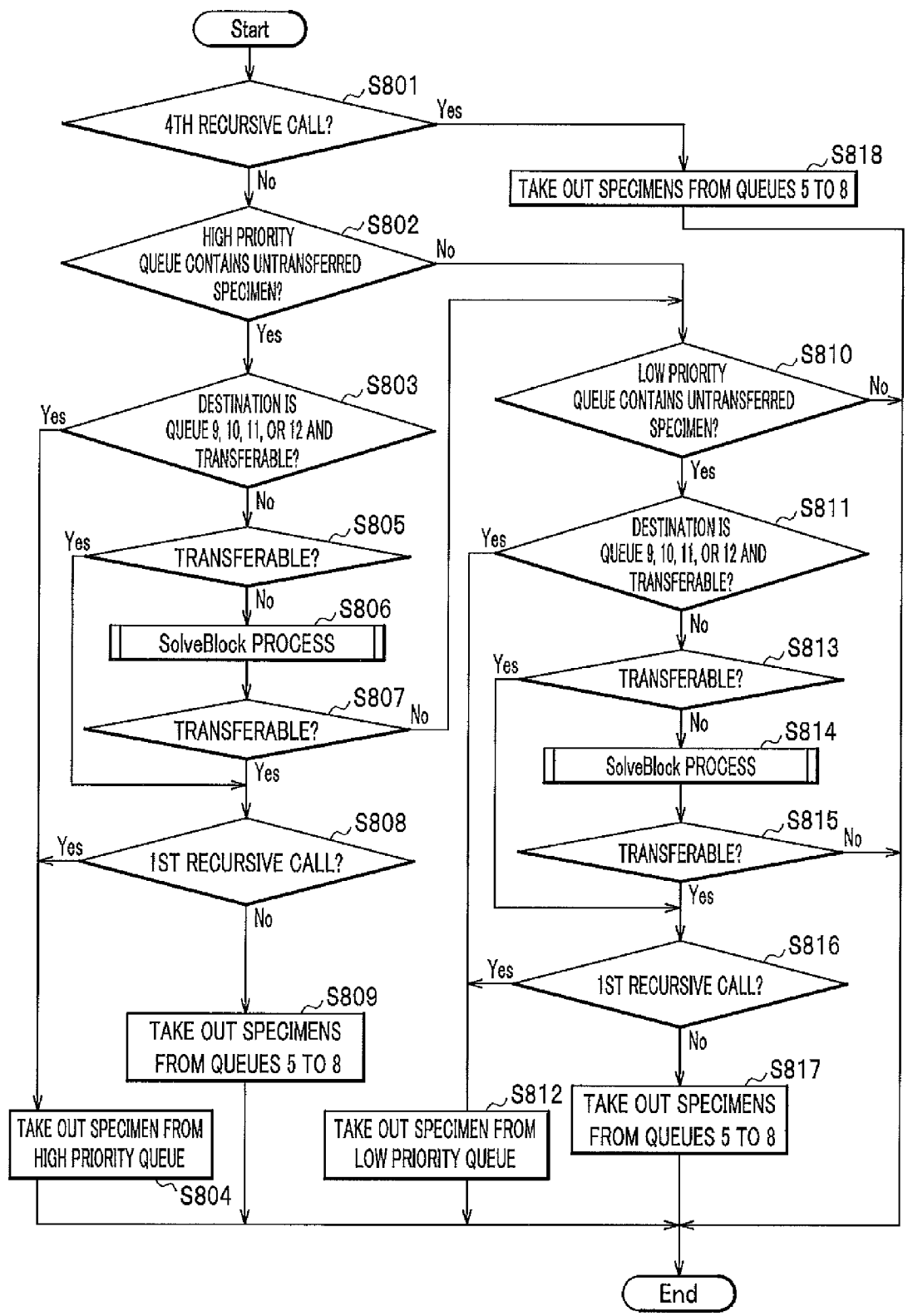
FIG. 29 is a flow chart of a SolveBlock process (priority determination processing) according to the second embodiment.

Next, a flow of the SolveBlock process is explained with reference to FIG. 29. In the SolveBlock process, specimens to be transferred in the respective blocks are determined in succession by recursively calling the SolveBlock process by itself.

At first (in step S801), it is determined whether or not the current call for the SolveBlock process is the fourth call.

When it is determined that the current call for the SolveBlock process is the fourth call (i.e., when no is determined), the operation goes to step S802. Otherwise (i.e., when yes is determined), the operation goes to step S818.

When the current call for the SolveBlock process is the fourth call (i.e., when no is determined in step S801), it is determined (in step S802) whether or not the high priority queue containing a specimen which has not yet been transferred exists.

When it is determined that the high priority queue contains a specimen which has not yet been transferred (i.e., when yes is determined), the operation goes to step S803. Otherwise (i.e., when no is determined), the operation goes to step S810.

When the high priority queue contains a specimen which has not yet been transferred (i.e., when yes is determined in step S802), it is determined (in step S803) whether or not the destination is one of the queues 9, 10, 11, and 12 and the specimen can be transferred to the destination (i.e., the queue has a space and any of the common portions is unused).

When it is determined that the destination is one of the queues 9, 10, 11, and 12 and the specimen can be transferred to the destination (i.e., when yes is determined), the operation goes to step S804. Otherwise (i.e., when no is determined), the operation goes to step S805.

When the destination is one of the queues 9, 10, 11, and 12 and the specimen can be transferred to the destination (i.e., when yes is determined in step S803), it is determined to transfer the specimen in order of the priority of the queue, and the processing is completed (in step S804).

When the destination is none of the queues 9, 10, 11, and 12 or the specimen cannot be transferred to the destination (i.e., when no is determined in step S803), it is determined whether or not the specimen can be transferred to the queue as the destination of the specimen (in step S805).

When it is determined that the specimen can be transferred (i.e., when yes is determined), the operation goes to step S808. Otherwise (i.e., when no is determined), the operation goes to step S806.

When the specimen cannot be transferred (i.e., when no is determined in step S805), the SolveBlock process is called with an identifier of the block to which the destination queue belongs (in step S806).

After that, it is determined again (in step S807) whether or not the specimen can be transferred.

When it is determined that the specimen can be transferred (i.e., when yes is determined), the operation goes to step S808. Otherwise (i.e., when no is determined), the operation goes to step S810.

When it is determined in step S805 or S807 that the specimen can be transferred (i.e., when yes is determined in step S805 or S807), it is determined (in step S808) whether or not the operation is performed in response to the first recursive call.

When it is determined that the operation is performed in response to the first recursive call (i.e., when yes is determined in step S808), the operation goes to step S804. Otherwise (i.e., when no is determined), the operation goes to step S809.

When the operation is not performed in response to the first recursive call (i.e., when no is determined in step S808), it is determined (in step S809) to transfer the specimen from one of the queues 5, 6, 7, and 8, and the processing is completed.

When it is determined in step S802 that the high priority queue contains no specimen which has not yet been transferred (i.e., when no is determined in step S802), or when it is determined in step S807 that the specimen cannot be transferred (i.e., when no is determined in step S807), it is determined (in step S810) whether or not a low priority queue contains a specimen which has not yet been transferred.

When it is determined that a low priority queue contains a specimen which has not yet been transferred (i.e., when yes is determined), the operation goes to step S811. Otherwise (i.e., when no is determined), the processing is completed.

When it is determined that a low priority queue contains a specimen which has not yet been transferred (i.e., when yes is determined in step S810), it is determined (in step S811) whether or not the destination of the specimen is one of the queues 9, 10, 11, and 12 and the specimen can be transferred to the destination.

When it is determined that the destination of the specimen is one of the queues 9, 10, 11, and 12 and the specimen can be transferred to the destination (i.e., when yes is determined), the operation goes to step S812. Otherwise (i.e., when no is determined), the operation goes to step S813.

When the destination is one of the queues 9, 10, 11, and 12 and the specimen can be transferred to the destination (i.e., when yes is determined in step S811), it is determined to transfer the specimen in the low priority queue, and the processing is completed (in step S812).

When it is determined that the destination is none of the queues 9, 10, 11, and 12 or the specimen cannot be transferred (i.e., when no is determined in step S811), it is determined whether or not the specimen can be transferred (in step S813).

When it is determined that the specimen can be transferred (i.e., when yes is determined), the operation goes to step S816. Otherwise (i.e., when no is determined), the operation goes to step s814.

When the specimen cannot be transferred (i.e., when no is determined in step S813), the SolveBlock process is called with an identifier of the block to which the destination queue belongs (in step S814).

After that, it is determined again whether or not the specimen can be transferred (in step S815).

When it is determined that the specimen can be transferred (i.e., when yes is determined), the operation goes to step S816. Otherwise (i.e., when no is determined in step S815), the processing is completed.

When it is determined in step S813 or S815 that the specimen can be transferred (i.e., when yes is determined in step S813 or S815), it is determined whether or not the operation is performed in response to the first recursive call (in step S816).

When it is determined that the operation is performed in response to the first recursive call (i.e., when yes is determined), the operation goes to step S812. Otherwise (i.e., when no is determined), the operation goes to step S817.

When the operation is not performed in response to the first recursive call (i.e., when no is determined in step S816), it is determined to transfer the specimen from one of the queues 5, 6, 7, and 8, and the processing is completed (in step S817).

According to the above processing, the take in/out scheduling unit 204 can determine from which queue to which queue the specimen is to be transferred.

Although the redirector 2108 illustrated in FIG. 23 has a planar arrangement, the processing is similar even in the case where the redirector has a configuration in which redirection mechanisms are three-dimensionally connected.

As the simplest example, it is possible to form the redirector with two planar configurations being arranged in parallel and each being identical to the planar arrangement of the four redirection mechanisms explained in the present embodiment, where the two planar configurations are connected with each other.

In addition, even in the case where a mechanism (such as a turning table) on which specimens can be placed and which can rotate is provided instead of the linear conveyor in the present embodiment, the common portions in the hardware cause variations in the processing performance when specimens are successively transferred in the same time zone.

In the above case, the priority control can be realized to equally receive specimens from the left, right, upper, and lower sides when priority is not assigned to any direction, and to receive specimens at high frequency from a preferred direction when priority is assigned to the preferred direction.

Further, according to the present embodiment, the method for adjusting the take-in and take-out includes: (1) the adjustment of the time of take-in from the input device; (2) the adjustment of the time of take-out from the centrifuge; (3) the adjustment of the time of take-out from the buffer device; and (4) the priority control in the redirectors.

However, the method may include only one of these features or two or more in combination, or may be combined with another control method.

Furthermore, the devices in which take-in and take-out are controlled may be limited.

<Additional Effect>

As explained above, according to this invention, the wait times in each wait region are simulated by using an initial take in/out schedule plan generated by the take in/out scheduling unit on the basis of the state of the existence of specimens in the automatic analysis system and an operational model of the automatic analysis system. When the wait time exceeds an allowable value, the TATs of urgent specimens can be brought within a predetermined time range by suppression of take-in and take-out of specimens, change in the order of take-in and take-out of the specimens, and the like Furthermore, since the TATs can be guaranteed even in the situations in which the amount of requests for tests is great, the laboratory technician can input specimens without concern for the order or timings of input of specimens.

Moreover, the efficiency in all of the testing operations can be increased by indicating to the laboratory technician and the like the state of congestion with specimens and the wait time and the time of completion of the tests of each specimen which are estimated on the basis of the state of congestion.

LIST OF REFERENCE NUMBERS 10, 20 automatic analysis system
100, 2100 testing device group
101, 2103 input device
102, 2104 centrifuge
103, 2105 decapper
104, 2106 aliquoter
105, 2107, 2111 linear conveyor
106A, 106B, 2110A, 2110B colorimetric analyzer
107, 2102 storing device
2101 recapper
2108, 2112 redirector
2109, 2113 buffer device
2114A, 2114B immunoassay device
108, 2115 device management server
109, 2116 laboratory-information management server
110, 2117 operations terminal
111, 2118 device information network
112, 2119 inspection information network
201 collection portion
202 mechanism control portion
203 tracking unit
204 take in/out scheduling unit
205 simulation unit
206 instruction unit
207 test-information providing unit
208 operations management unit
291 transfer route DB (information of the transfer route)
292 device model DB
293 test request DB
294 parameters DB
291A transfer route information
292A, 292B device model information
293A request information
294A scheduling parameters
301 (A to E), 2301 conveyor line
302 (A to H), 2302 redirection mechanism
303 (A to H), 2303 stopper
304 (A to I), 2304 specimen detection sensor
305 processing mechanism
M271 sensor value
M272 take in/out instruction
M273 initial condition information
M274 processing item information
D281 wait region information
D282 take in/out schedule plan
D283 congestion progress information
D284 take in/out schedule
T100 item group definition list
T200 route definition table
T300 item-route correspondence table
T400 model object (operational model)
T500 state definition table
T600 state transition table
T700 test request information table
T800 scheduling parameter table
T900 connection definition table
T1000 state definition table for redirectors
T2000 preferred-queue determination rule table

The invention claimed is:

1. An automatic analysis system comprising:
an operations terminal;
a device management server communicatively coupled to the operations terminal;
a laboratory-information management server communicatively coupled to the device management server; and
one or more testing device groups;
wherein the operations terminal, device management server and the laboratory information server each include a respective central processing unit (CPU) and a respective memory coupled to the respective CPU;
wherein the device management server is configured to:
constantly determine a determined current position of each specimen in the devices by using an order of take-in and take-out of one or more specimens that are input in the automatic analysis system, information on predetermined transfer routes according to details of tests, and signals of specimen detection sensors arranged in each of the one or more testing device groups,
constantly provide the operation terminal with the determined current position,
constantly calculate a staying time of each specimen in one of wait regions up to a predetermined length of period from current time in the devices by simulating, based on operational models of the devices, an operation of each device in accordance with a take in/out schedule plan assuming an initial state in which each specimen is at the determined current position; and
repetitively evaluate a final take in/out schedule by: producing an initial take in/out schedule plan for taking in or taking out an urgent specimen in preference to a normal specimen; performing the simulation in accordance with the initial schedule plan; and, when the staying time of one of the specimens in one of the wait regions exceeds an allowable staying time in the wait region, correcting, in the initial take in/out schedule plan, the timing or the order of take-in and take-out of at least one of the specimens other than the specimen of which staying time exceeds the allowable staying time,
remove one or more processed specimens using a robotic arm communicatively coupled to the device management server based on the final take in/out schedule;
wherein:
the operational models are each defined by states of a corresponding one of the devices and state transitions, the states of the device being defined by a number of specimens in each of the wait regions in the device, each state transition prescribing a transition condition, a necessary processing time, and a next state, for a corresponding one of the states of the device, and
the operational models include an operational model for an aliquoter, and the states of the device and the state transitions defining the operational model of the aliquoter include a definition of an operation for producing one or more secondary specimens according to an aliquot ratio.

2. The automatic analysis system according to claim 1, wherein the operational models include an operational model for a device having a confluence of transfer paths, and wherein the states of the device and the state transitions defining the operational model of the device having a confluence of transfer paths include a definition of an operation for controlling an order of take-in to the confluence according to the number of specimens in each of wait regions adjacent and directed to the confluence.

3. The automatic analysis system according to claim 2, wherein the states of the device defining the operational model of the device having a confluence of transfer paths are defined by a combination of a state of use of the confluence and the number of specimens in each of the wait regions adjacent and directed to the confluence.

4. The automatic analysis system according to claim 1, wherein the correction of the timing or the order of take-in and take-out of the specimen is made by delaying a time of take-in and take-out of a specimen which is planned to be taken in and out before the specimen of which staying time exceeds the allowable staying time.

5. The automatic analysis system according to claim 4, when the staying times of multiple specimens in the wait regions in the devices exceed allowable staying times, the correction of the timing or the order of take-in and take-out of the specimen is made by delaying a time of take-in and take-out of a specimen which is planned to be taken in and out before one of the multiple specimens of which staying times exceeds corresponding one of the allowable staying times at an earliest time.

6. The automatic analysis system according to claim 1, wherein, when the specimen of which staying time exceeds the allowable staying time does not need processing by a device which processes multiple specimens at once, the correction of the timing or the order of take-in and take-out of the specimen is made by delaying a time of take-out of a normal specimen which is processed by the device in a time zone in which the specimen of which staying time exceeds the allowable staying time is transferred in a vicinity of the device.

7. The automatic analysis system according to claim 1, wherein, when the specimen of which staying time exceeds the allowable staying time stays in a vicinity of a device having a confluence of transfer paths, the correction of the timing or the order of take-in and take-out of the specimen is made by delaying a time of take-out of a normal specimen staying in an analyzer or a buffer device which is connected to the device.

8. The automatic analysis system according to claim 1, wherein, when the specimen of which staying time exceeds the allowable staying time stays in a vicinity of a device having a confluence of transfer paths, the correction of the timing or the order of take-in and take-out of the specimen is made by causing a specimen staying in one of take-in directions toward the device to be preferentially transferred, when the staying time of the specimen staying in the one of the take-in directions is estimated to be the greatest among all specimens staying in the take-in directions toward the device.

9. The automatic analysis system according to claim 1, wherein the allowable staying time is generated by dividing an allowable delay time among all wait regions in a transfer route predetermined according to details of requested tests, and the allowable delay time is set with reference to a shortest processing time of a specimen through the transfer route.

10. A device management server for specimen analysis, comprising:

a CPU comprising:
a tracking unit;
a simulation unit;
an instruct unit; and
a scheduling unit;
wherein the tracking unit, constantly determines:
a determined current position of each specimen by using an order of take-in and take-out of one or more specimens that are input in an automatic analysis system, information on predetermined transfer routes according to details of tests, and signals of specimen detection sensors arranged in each device, and
constantly provides an operation terminal with the determined current position;
wherein the simulation unit constantly estimates a staying time of each specimen in one of wait regions up to a predetermined length of period from current time in the devices by simulating, based on operational models of the devices, an operation of each device in accordance with a take in/out schedule plan assuming an initial state in which each specimen is at the determined current position; and
wherein the scheduling unit constantly evaluates a final take in/out schedule by:
producing an initial take in/out schedule plan for taking in or taking out an urgent specimen in preference to a normal specimen;
a simulation in accordance with the initial schedule plan; and, when a staying time of one of the specimens in one of the wait regions exceeds an allowable staying time in the wait region, correcting, in the initial take in/out schedule plan, a timing or an order of take-in and take-out of at least one of the specimens other than the specimen of which staying time exceeds the allowable staying time;
wherein the instruct unit removes one or more processed specimens using a robotic arm based on the final take in/out schedule;
wherein:
the operational models are each defined by states of a corresponding one of the devices and state transitions, the states of the device being defined by a number of specimens in each of the wait regions in the device, each state transition prescribing a transition condition, a necessary processing time, and a next state, for a corresponding one of the states of the device, and
the operational models include an operational model for an aliquoter, and the states of the device and the state transitions defining the operational model of the aliquoter include a definition of an operation for producing one or more secondary specimens according to an aliquot ratio.

* * * * *